US008029832B2

(12) United States Patent
Kwak et al.

(10) Patent No.: US 8,029,832 B2
(45) Date of Patent: Oct. 4, 2011

(54) OBESITY AND METABOLIC SYNDROME TREATMENT WITH TANSHINONE DERIVATIVES WHICH INCREASE METABOLIC ACTIVITY

(75) Inventors: Taehwan Kwak, Gyeonggi-do (KR); Myunggyu Park, Gyeonggi-do (KR)

(73) Assignees: MD Bioalpha Co., Ltd. (KR); KT&G Co., Ltd. (KR)

( * ) Notice: Subject to any disclaimer, the term of this patent is extended or adjusted under 35 U.S.C. 154(b) by 175 days.

(21) Appl. No.: 12/555,233

(22) Filed: Sep. 8, 2009

(65) Prior Publication Data

US 2010/0029760 A1  Feb. 4, 2010

Related U.S. Application Data

(63) Continuation of application No. 10/584,983, filed on Apr. 12, 2007, now abandoned.

(30) Foreign Application Priority Data

| Dec. 30, 2003 | (KR) | 10-2003-0099556 |
|---|---|---|
| Dec. 30, 2003 | (KR) | 10-2003-0099557 |
| Dec. 30, 2003 | (KR) | 10-2003-0099657 |
| Dec. 30, 2003 | (KR) | 10-2003-0099658 |
| May 21, 2004 | (KR) | 10-2004-0036195 |
| May 21, 2004 | (KR) | 10-2004-0036197 |
| Jun. 30, 2004 | (KR) | 10-2004-0050200 |

(51) Int. Cl.
    *A61K 36/537* (2006.01)
(52) U.S. Cl. ..................................................... 424/746
(58) Field of Classification Search .................. None
    See application file for complete search history.

(56) References Cited

U.S. PATENT DOCUMENTS

2003/0114431 A1  6/2003  Girouard

FOREIGN PATENT DOCUMENTS

| KR | 1020000027306 | 5/2000 |
| KR | 1020010019147 | 3/2001 |
| KR | 1020040084482 | 10/2004 |

OTHER PUBLICATIONS

Stimulation of AMP-Activated Protein Kinase (AMPK) Is Associated with Enhancement of Glut 1-Mediated Glucose Transport; Author: Abbud, et al.;Arch. Biochem. Biophys.;vol. 380,pp. 347-352,2000.
Regulation of muscle GLUT-4 transcription by AMP-activated protein kinase; Author: Zheng, et al.; J. Appl. Physiol.; vol. 91, pp. 1073-1083, 2001.
Coordinate Regulation of Malonyl-CoA Decarboxylase, sn-Glycerol-3-phosphate Acyltransferase, and Acetyl0CoA Carboxylase by AMP-actvated Protein Kinase in Rat Tissues in Response to Exercise; Author: Park, et al.; J. Biol. Chem.; vol. 227,pp. 32571-32577, 2002.
Phosphorylation-activity relationships of AMPK and acetyl-CoA carboxylase in muscle; Author: Park, et al.;J. Appl. Physiol; vol. 92,pp. 2475-2482,2002.
Mechanism for Fatty Acid "Sparing" Effect on Glucose-induced Transcription; Author: Kawagachi, et al.; J. Biol. Chem.; vol. 277, pp. 3829-3835,2002.
Inhibition of Inducible Nitric-oxide Synthase by Activators of AMP-activated Protein Kinase; Author: Pilon, et al.; J. Biol. Chem.; vol. 279,pp. 20767-20774, 2004.
AMP Kinase and Malonyl-COA: Targets for Therapy of the Metaolic Syndrome; Author: Ruderman, et al.; Nature drug discovery; vol. 3,pp. 340-351, Apr. 2004.
PPARy coactivator-1a expression during thyroid hormone-and contractile activity-induced mitochondrial adaptations; Author: Irrcher, et al.;Am. J. Physiol. Cell Physiol.;vol. 284, c1669-c1677, 2003.
AMP-activated protein kinase phosphorylation of endothelial NO synthase; Author: Chen, et al.; FEBS Letters 443,pp. 285-289, 1999.
Coordinated reduction of genes of oxidative metabolism in humans with insulin resistance and diabetes: Potential role of PGC1 and NRF1, Author: Patti, et al.;PNAS ;vol. 100, No. 14; pp. 8466-8471, 2003.
Inhibitory Activity of Diacylglycerol Acyltransferase by Tanshinones from the Root Salvia miltiorrhiza; Author: Ko, et al; Arch. Pharm. Res.; vol. 25,pp. 446-448, 2002.
Dihydrosotanshinone I Protects Against Menadione-Induced Toxicity in a Primary Culture of Rat Hepatocytes; Author: Ip, et al.; Planta Med.; 68,pp. 1077-1081, 2002.
Aldose Reductase Inhibitory Constituents of the Root of Salvia miltiorhiza BUNGE; Author: Tezuka, et al.; Chem. Pharm. Bull.; vol. 45, No. 8; pp. 1306-1311,1997.
Possible Aktive Components of Tan-Shen (Salvia miltiorrhiza) for Protection of the Myocardium Against Ischemia-Induced Derangements; Author: Yagi, et al.; Planta Med.; vol. 55; pp. 51-54, 1989.
Role of UCP2 and UCP3 in Nutrition and Obesity;Author: Nagy, et al.; Nutrition; vol. 20, pp. 139-144,2004.
Phosphorylation and activation of heart PFK-2 by AMPK has a role in the stimulation of glycolysis during ischaemia; Author: Marsin, et al.; Curr. Biol.; vol. 10,pp. 1247-1255, 2000.
5-Aminoimidazole-4-Carboxamide Riboside Mimics the Effects of Insulin on the Expression of the 2 Key Gluconeogenic Genes PEPCK and Glucose-6-Phosphatase; Author: Lochead, et al.; Diabetes; vol. 49,pp. 896-903,2000.
Mitochondrial fission in apoptosis, neurodegeneration and aging; Author: Bossy-Wetzel, et al.;Curr. Opin. Cell Biol.; vol. 15, pp. 706-716, 2003.
Mitochondrial Dysfunction in the Elderly: Possible Role in Insulin Resistance; Author: Peterson, et al.; Science; vol. 300, pp. 1140-1142, 2003.
Decreased mitochondrial DNA content in peripheral blood precedes the developement of non-insulin-dependent diabetes mellitus; Author: Lee, et al.; Diabetes Res. Clin. Pract.; vol. 42,pp. 161-167, 1998.
Mechanisms Controlling Mitochondrial Biogenesis and Respiration through the Thermogenic Coactivator PGC-1; Author: Wu, et al.; Cell; vol. 98, pp. 115-124,1999.

(Continued)

Primary Examiner — Susan Hoffman
(74) Attorney, Agent, or Firm — Cantor Colburn LLP

(57) ABSTRACT

The present invention relates to a composition for preventing and treating metabolic syndrome, containing tanshinone derivatives as an effective ingredient. More specifically, the present invention relates to a composition for preventing and treating metabolic syndrome, containing tanshinone derivatives that exhibit superior activity in enhancing metabolic activity, as an effective ingredient.

8 Claims, 15 Drawing Sheets

OTHER PUBLICATIONS

Effects of Tanshinone VI on the Hypertrophy of Cardiac Myocytes and Fibrosis of Cardiac Fibroblasts fo Neonatal Rats; Author: Maki, et al.; Planta Med.; vol. 68, pp. 1103-1107,2002.

Tanshinones inhibit mast cell degranulation by interfering with IgE receptor-mediated tyrosine phosphorylation of PLCgamma2 and MAPK; Author: Choi, et al.; Planta Med.; vol. 70,pp. 178-180, 2004.

Novel Diterpenoid acetylcholinesterase Inhibitors from Salvia miltiorhiza; Author: Ren, et al.; Planta Med.;vol. 70, pp. 201-204, 2004.

Sodium tanshinone IIA sulfonate derived from Danshen (Salvia miltiorrhiza) attenuates hypertrophy induced by angiotensin II in cultured neonatal rat cardiac cells; Author: Takahashi, et al.; Biochemical Pharmacology; vol. 64, pp. 745-750, 2002.

Antibacterial Activities of Cryptotanshinonee and Dihydrotanshinone I from a Medicinal Herb, Salvia miltiorrhiza Bunge; Author: Lee, et al.; Biosci. Biotechnol. Biochem.; vol. 63(12), pp. 2236-2239,1999.

Inhibition of interleukin-12 and interferon-y production in imnune cells by tanshinones from Salvia miltiorrhiza; Author: Kang, et al.; Immunopharmacology; vol. 49, pp. 355-361,2000.

Sodium tanshinone IIA sulfonate mediates electron transfer reaction in rat heart mitochondria; Author: Zhou, et al.; Biochemical Pharmacology; vol. 65, pp. 51-57, 2003.

Tanshinone (Salvia miltiorrhzae Extract) Preparations Attenuate Aminoglycoside-Induced Free Radical Formation In Vitro and Ototoxicity In Vivo; Author; Wang, et al.; Antimicrobial Agent & Chemotherapy; vol. 47, No. 6; pp. 1836-1841, Jun. 2003.

International Search Report ; International Applicaton No. PCT/KR2004/003546; International Filing date: Dec. 30, 2004; Date of Mailing Mar. 11, 2005.

Written Opinion for Application No. PCT/KR2004/003546 dated Dec. 30, 2004.

International Preliminary Exam Report for Application No. PCT/KR2004/003546 dated Dec. 30, 2004.

Control   Crytotanshinone (30uM)   15,16-dihydrotanshinone (5uM)

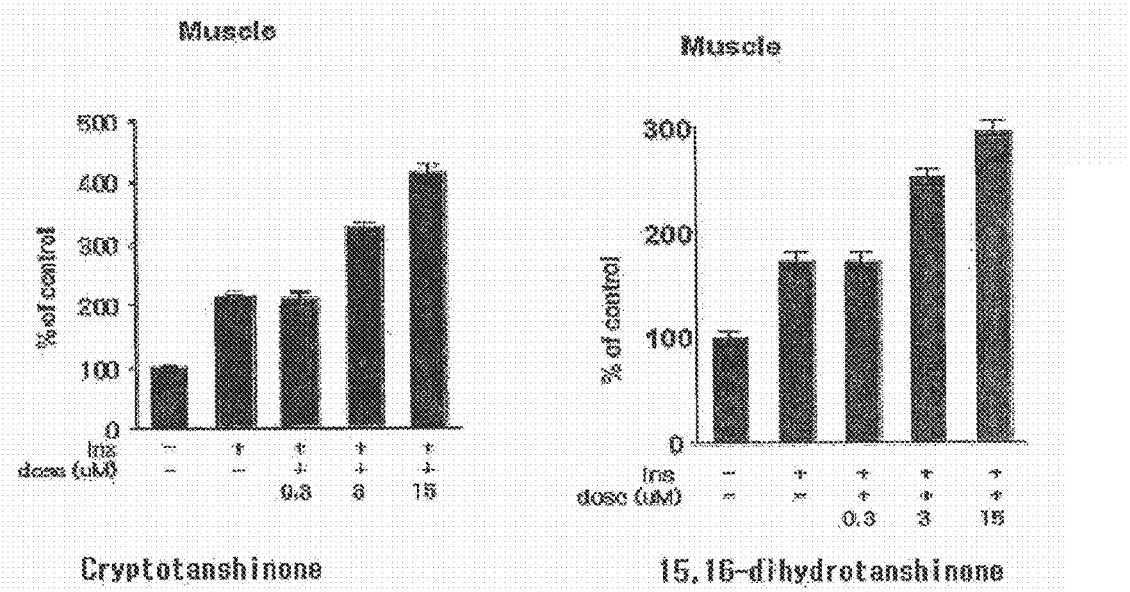

|  | Initial body weight(g) | Final body weight(g) | Decrease in body weight(%) |
|---|---|---|---|
| Control | 50±0.23 | 52±0.5 | −4±0.04 |
| Cryptotanshinone | 53±0.073 | 48.8±0.22 | 8±0.32 |
| 15,16-dihydrotanshinone | 53±0.07 | 49±0.3 | 7±0.27 |
| Tanshinone II A | 52±0.25 | 47±0.3 | 9±0.01 |
| Tanshinone I | 54±0.4 | 50±0.05 | 7±0.24 |

|  | Control | Cryptotanshinone | 15,16-dihydrotanshinone |
|---|---|---|---|
| Fat (g/g.liver) | 0.21±0.03 | 0.15±0.08 | 0.18±0.06 |
| Triglyceride (mg/g.liver) | 86.3±19.5[ab] | 32.2±18.8[c] | 37.2±17.2[c] |
| GOT(u/dL) | 62.5±23.1[a] | 22.3±7.2[c] | 27.3±7.2[c] |
| GPT(u/dL) | 47.0±10.6[a] | 20.1±6.1[b] | 22.1±7.1[b] |
| Cholesterol (mg/g.liver) | 5.8±1.6[ab] | 5.5±2.9 | 5.6±2.9 |

|  | Control | Cryptotanshinone | 15,16-dihydrotanshinone |
|---|---|---|---|
| Triglyceride (mg/dL) | 260.6±24.3$^a$ | 153.6±14.6$^b$ | 167.2±14.6$^b$ |
| Cholesterol (mg/dL) | 163.5±8.4$^{ab}$ | 120.1±72.1$^b$ | 135.1±73.1$^b$ |
| Blood glucose (mg/dL) | 168.4±55.0$^{ab}$ | 122.4±67.1$^b$ | 127.4±67.1$^b$ |

FIG. 16

|  | Initial blood glucose (mg/dl) | Final blood glucose (mg/dl) | Decrease in blood glucose (%) |
|---|---|---|---|
| Control | 400±1.24 | 430±5.6 | -7.5±0.2 |
| Cryptotanshinone | 400±2.56 | 200±4.7 | 50±0.33 |
| 15,16-dihydrotanshinone | 410±0.6 | 250±4.9 | 61±0.89 |

FIG. 17

|   | Items | Con. (uM) | AMPK act. |
|---|---|---|---|
| 1 | DMSO | 5% | 1 |
|   | Tanshinone II A(5uM)+Tanshinone I (5uM) | 10 | 1.7 |
|   | Tanshinone II A | 10 | 1.4 |
|   | Tanshinone I | 10 | 1.3 |
| 2 | DMSO | 5% | 1 |
|   | Tanshinone II A(5uM) +Cryptotanshinone(5uM) | 10 | 1.9 |
|   | Tanshinone II A | 10 | 1.4 |
|   | Cryptotanshinone | 10 | 1.5 |
| 3 | DMSO | 5% | 1 |
|   | Tanshinone II A(5uM) +15,16-dihydrotanshinone(5uM) | 10 | 2.0 |
|   | Tanshinone II A | 10 | 1.4 |
|   | 15,16-dihydrotanshinone | 10 | 1.5 |
| 4 | DMSO | 5% | 1 |
|   | Tanshinone I (5uM) +Cryptotanshinone(5uM) | 10 | 1.9 |
|   | Tanshinone I | 10 | 1.3 |
|   | Cryptotanshinone | 10 | 1.6 |
| 5 | DMSO | 5% | 1 |
|   | Tanshinone I (5uM) +15,16-dihydrotanshinone(5uM) | 10 | 2.0 |
|   | Tanshinone I | 10 | 1.3 |
|   | 15,16-dihydrotanshinone | 10 | 1.6 |
| 6 | DMSO | 5% | 1 |
|   | Cryptotanshinone(5uM) +15,16-dihydrotanshinone(5uM) | 10 | 2.2 |
|   | Cryptotanshinone | 10 | 1.5 |
|   | 15,16-dihydrotanshinone | 10 | 1.6 |

FIG. 18

| Items | Mixing ratio | Con. (uM) | AMPK activity |
|---|---|---|---|
| DMSO | | 5% | 1 |
| Tanshinone I + Cryptotanshinone | 1:4 | 10 | 2.0 |
| | 1:1 | 10 | 1.8 |
| | 4:1 | 10 | 1.6 |
| Tanshinone I + 15,16-dihydrotanshinone | 1:4 | 10 | 2.3 |
| | 1:1 | 10 | 1.8 |
| | 4:1 | 10 | 1.7 |
| Cryptotanshinone + 15,16-dihydrotanshinone | 1:4 | 10 | 2.3 |
| | 1:1 | 10 | 2.0 |
| | 4:1 | 10 | 2.0 |

FIG. 19

| | Items | Con. (uM) | AMPK activity |
|---|---|---|---|
| 1 | DMSO | 5% | 1 |
| | Tanshinone II A(3.3uM) +Tanshinone I (3.3uM) +Cryptotanshinone(3.4uM) | 10 | 1.8 |
| | Tanshinone II A | 10 | 1.4 |
| | Tanshinone I | 10 | 1.3 |
| | Cryptotanshinone | 10 | 1.5 |
| 2 | DMSO | 5% | 1 |
| | Tanshinone II A(3.3uM) +Tanshinone I (3.3uM) +15,16-dihydrotanshinone(3.4uM) | 10 | 1.9 |
| | Tanshinone II A | 10 | 1.4 |
| | Tanshinone I | 10 | 1.3 |
| | 15,16-dihydrotanshinone | 10 | 1.6 |
| 3 | DMSO | 5% | 1 |
| | Tanshinone I (3.3uM) +Cryptotanshinone(3.3uM) +15,16-dihydrotanshinone(3.4uM) | 10 | 2.1 |
| | Tanshinone I | 10 | 1.3 |
| | Cryptotanshinone | 10 | 1.6 |
| | 15,16-dihydrotanshinone | 10 | 1.7 |
| 4 | DMSO | 5% | 1 |
| | Cryptotanshinone(3.3uM) +15,16-dihydrotanshinone(3.4uM) +Tanshinone II A(3.3uM) | 10 | 2.2 |
| | Cryptotanshinone | 10 | 1.6 |
| | 15,16-dihydrotanshinone | 10 | 1.7 |
| | Tanshinone II A | 10 | 1.4 |

FIG. 20

| Composition rate | | Initial body weight (g) | Final body weight (g) | Decrease in body weight(%) |
|---|---|---|---|---|
| Tetrahydrophe-nanthrene deriv. | Phenanthrene derivative | | | |
| 10 | 0 | 51.3±0.86 | 50.5±0.62 | 1.5 |
| 10 | 1 | 50.6±0.92 | 49.6±1.2 | 2 |
| 5 | 1 | 51.4±0.85 | 48.7±0.83 | 5.3 |
| 2.5 | 1 | 52.3±0.74 | 47.8±1.1 | 8.6 |
| 1 | 1 | 49.8±0.95 | 43.6±2.3 | 12.5 |
| 1 | 2.5 | 50.2±0.74 | 44.4±1.8 | 11.5 |
| 1 | 5 | 48.8±0.93 | 44.88±1.5 | 8.2 |
| 1 | 10 | 51.8±0.68 | 48.54±1.9 | 6.3 |
| 0 | 10 | 50.8±0.73 | 47.96±0.69 | 5.6 |
| Control | | 49.8±0.84 | 51.89±1.2 | -4.2 |

OBESITY AND METABOLIC SYNDROME TREATMENT WITH TANSHINONE DERIVATIVES WHICH INCREASE METABOLIC ACTIVITY

This application is a continuation of U.S. patent application Ser. No. 10/584,983, filed Apr. 12, 2007, now abandoned.

FIELD OF THE INVENTION

The present invention relates to a composition for preventing and treating metabolic syndrome, containing tanshinone derivatives as an effective ingredient. More specifically, the present invention relates to a composition for preventing and treating metabolic syndrome, containing tanshinone derivatives that exhibit superior activity in enhancing metabolic activity, as an effective ingredient.

BACKGROUND OF THE INVENTION

Metabolic syndrome refers to syndrome involving health risk factors such as hypertriglyceridemia, hypertension, glycometabolism disorder, blood coagulation disorder and obesity. Metabolic syndrome itself is not fatal, but indicates a predisposition to severe diseases such as diabetes and ischemic cardiovascular diseases, and has emerged as the most threatening diseases among modern people. Metabolic syndrome was once known by various other names including Syndrome X, due to lack of knowledge about causes of such syndrome, but was officially designated as Metabolic Syndrome or Insulin Resistance Syndrome through Adult Treatment Program III (ATP III) enacted by the WHO and the National Heart, Lung, and Blood Institute of the NIH.

The criteria proposed by the Third Report of the National Cholesterol Education Program (NCEP) Expert Panel on Detection, Evaluation, and Treatment of High Blood Cholesterol in Adults (Adult Treatment Panel III), published in 2001, are the most current and widely used for diagnosing the metabolic syndrome. According to the ATP III criteria, individuals are diagnosed with the metabolic syndrome by the presence of three or more of these components: 1) A waistline of 40 inches (102 cm) or more for men and 35 inches (88 cm) or more for women (central obesity as measured by waist circumference), 2) A triglyceride level above 150 mg/dl, 3) A high density lipoprotein level (HDL) less than 40 mg/dl (men) or under 50 mg/dl (women), 4) A blood pressure of 130/85 mm Hg or higher and 5) A fasting blood glucose (sugar) level greater than 110 mg/dl. For eastern people, the criteria for central obesity was slightly adjusted to a waistline of 90 cm or more for men and 80 cm or more for women. Recent research has reported that under such criteria, around 25% of Korean people suffer from metabolic syndrome. Insulin resistance refers to a phenomenon wherein, even though insulin is normally secreted in vivo, insulin does not induce sufficient supply of glucose to cells. Therefore, glucose in the blood cannot enter cells, thus causing hyperglycemia, and thereby cells cannot perform normal functions due to a shortage of glucose, leading to the manifestation of metabolic syndrome.

At present, there are no drugs available for the treatment of metabolic syndrome. Attempts have been made to treat metabolic syndrome using therapeutic agents for diabetes, hyperlipidemia and hypertension, but these drugs have limited effectiveness in treating metabolic syndrome as the drug. As currently available drugs, metformin, drugs belonging to the TZD (thiazolidinediones) family, glucosidase inhibitors, dual PPARγ/α agonists and DDP (Dipeptidyl peptidase) IV inhibitors, which are used for the treatment of diabetes, have received a great deal of attention as promising drugs for treating metabolic syndrome. In addition, a great deal of interest has been directed to isoforms of apo A-I and related peptides thereof, which are targets of anti-blood pressure drugs and anti-hyperlipidemic drugs, and CETP (Cholesterol ester transport protein) inhibitors.

Known factors that are directly or indirectly associated with causes and treatment of metabolic syndrome include physical exercise, dietary habit and type, body weight, blood glucose, triglyceride levels, cholesterol levels, insulin resistance, adiponectin, leptin, AMPK activity, sex hormones such as estrogen, genetic factors and in vivo malonyl-CoA concentration.

At present, the most effective way to fight the conditions associated with metabolic syndrome is known to be getting more exercise and losing weight, and dietary control. All of the current ways of fighting metabolic syndrome share in common the fact that they facilitate energy metabolism, thus resulting in maximized consumption of surplus energy in the body leading to prevention of energy accumulation. Due to high calorie intake from processed foods and fast foods, compared to insufficient exercise, surplus energy is accumulated in the form of fat and thereby becomes an underlying cause of various diseases including metabolic disorders. Effectively eliminating such surplus energy is considered a method for treating metabolic disorders. Increasing metabolic activity is essential to effectively eliminate surplus energy. For this purpose, it is believed that there is an essential need for inhibition of fat synthesis, inhibition of gluconeogenesis, facilitation of glucose consumption, facilitation of fat oxidation, facilitation of biogenesis of mitochondria which is a central apparatus of energy metabolism and activation of factors involved in metabolism activation. Activation factors linked to promotion of metabolism include, for example, AMP-activated protein kinase (AMPK), peroxisome proliferator-activated receptor gamma coactivator 1α (PGC-1α), glucose transporter 1 and 4 (GLUT 1 and 4), carnitine palmitoyltransferase 1 (CPT 1), uncoupling protein 1, 2 and 3 (UCP-1, 2 and 3), and acetyl-CoA carboxylase I and II (ACC I and II), which play an important role in energy metabolism.

Such factors perform the following main functions in energy metabolism, in relation to metabolic disorders.

1. Glycometabolism

In muscle tissues and myocardial tissues, AMPK promotes muscle contraction and thereby facilitates uptake of glucose, which in turn activates GLUT 1, or induces migration of GLUT 4 to a plasma membrane, regardless of insulin action, resulting in increased transport of glucose into cells (Arch. Biochem. Biophys. 380, 347-352, 2000, J. Appl. Physiol. 91, 1073-1083, 2001). After increase of glucose uptake, AMPK activates hexokinase, thereby increasing flux of glycometabolism processes and simultaneously inhibiting glycogen synthesis. It is known that in myocardial tissues during ischemia, AMPK activates 6-phosphofructo-2-kinase (PFK-2) via a phosphorylation process, thus resulting in activation of a metabolic cascade leading to increased flux of glycometabolism (Curr. Biol. 10, 1247-1255, 2000). In addition, activation of AMPK in the liver inhibits release of glucose from hepatocytes. Meanwhile, it was confirmed that activity of phosphoenolpyruvate carboxykinase (PEPCK) and glucose-6-phosphatase, which are enzymes of gluconeogenesis, was arrested by AMPK (Diabetes 49, 896-903, 2000), indicating that AMPK independently inhibits release of glucose from the liver, regardless of insulin, thus being involved in modulation of blood glucose level.

2. Mitochondrial Biogenesis

One important function of mitochondria is to carry out oxidative phosphorylation, which converts energy produced from fuel metabolites such as glucose and fatty acids into ATP. Functional mitochondrial alterations may effect pathogenesis of degenerative diseases associated with senescence, such as diabetes mellitus, cardiovascular diseases, Parkinson's disease and senile dementia (Curr. Opin. Cell Biol. 15, 706-716, 2003). Peterson, et al (Science 300, 1140-1142, 2003) has reported that oxidative phosphorylation functions of mitochondria were weakened by about 40% in the elderly, suggesting the possibility that deteriorated mitochondrial function is a probable pathogenic cause of insulin resistance syndrome. Lee et al (Diabetes Res. Clin. Pract. 42, 161-167, 1998) have confirmed that decreased mitochondrial DNA content in peripheral blood precedes the development of diabetes mellitus. Biogenesis of mitochondria in muscles is known to be promoted by an adaptive reaction in which metabolic activity of oxidative phosphorylation of muscle cells is increased by continuous energy depletion and exercise.

Meanwhile, peroxisome proliferator-activated receptor gamma coactivator 1α (PGC-1α) is known to be a co-activator promoting transcription of nuclear DNA and is known to play important roles in glucose metabolism, mitochondrial biogenesis, muscle fiber specialization and adaptive thermogenesis as main functions. It was confirmed that increased expression of PGC-1α facilitates an increase in the copy number of mitochondrial DNA and mitochondrial proliferation (Cell, 98, 115-124, 1999).

It was suggested that overexpression of UCP-2 and UCP-3 in the mouse model results in a decreased number of adipocytes, increased metabolic rate and increased oxygen consumption, and thus UCP-2 and UCP-3 play an important role in energy metabolism and obesity control (Nutrition, 20, 139-144, 2004).

3. Control of Fat Metabolism

Referring to a mechanism in which AMPK participates in fat metabolism, AMPK is known to induce phosphorylation of acetyl-CoA carboxylase which in turn inhibits fatty acid synthesis, thus resulting in decreased intracellular concentrations of malonyl-CoA that is an intermediate in a fatty acid synthesis process and is an inhibitor of carnitine palmitoyltransferase I (CPT I), leading to promotion of fatty acid oxidation. CPT I is an enzyme essential for a process wherein fatty acids enter mitochondria and are oxidized, and is known to be modulated by intracellular concentration of malonyl-CoA. In addition, AMPK is known to inhibit activity of HMG-CoA reductase and glycerol phosphate acyl transferase (GPAT), involved in cholesterol and triacylglycerol synthesis, through phosphorylation (J. Biol. Chem. 277, 32571-32577, 2002, Appl. Physiol. 92, 2475-2482, 2002). Meanwhile, it was found that activation of AMPK in the liver inhibits the activity of pyruvate kinase, fatty acid synthase and ACC through phosphorylation of carbohydrate-response-element-binding protein (ChREBP) (J. Biol. Chem. 277, 3829-3835, 2002).

As described above, activators related to metabolism are known to play central roles in energy metabolism of glucose, protein, and fat in vitro and in vivo. Neil et al (Nature drug discovery, 3(April), 340, 2004) asserted that AMPK and Malonyl-CoA are targets for therapeutic treatment of metabolic syndrome, and patients suffering from metabolic syndrome are characterized by insulin resistance, obesity, hypertension, dyslipidemia, and dysfunction of pancreatic beta cells, type I diabetes mellitus and manifestation of arteriosclerosis. It was hypothesized that a common feature linking these multiple abnormalities is dysregulation of AMPK/Malonyl-CoA fuel-sensing and signaling network. It was proposed that such dysregulation leads to alterations in cellular fatty-acid metabolism that in turn cause abnormal lipid accumulation, cellular dysfunction and ultimately disease. Evidence is also presented that factors that activate AMPK and/or reduce malonyl-CoA levels might reverse these abnormalities and syndromes or prevent them from occurring.

Genevieve et al (J. Biol. Chem. 279, 20767-74, 2004) have reported that activation of AMPK inhibits activity of an iNOS enzyme that is a inflammation mediator in chronic inflammatory conditions or endotoxin shock, including obesity-related diabetes and thus will be effective for developing new medicines having a mechanism capable of enhancing insulin sensitivity. In addition, they have reported that inhibition of iNOS activity is effected by activation of AMPK, and thus this finding is clinically applicable to diseases such as septicemia, multiple sclerosis, myocardial infarction, inflammatory bowel diseases and pancreatic beta-cell dysfunction. Zingping et al (FEBS Letters 443, 285-289, 1999) have reported that AMPK activates endothelial NO synthase through phosphorylation, in the presence of Ca-calmodulin in muscle cells and myocardial cells of rats. This represents that AMPK is implicated in cardiac diseases including angina pectoris. Alan D et al (Nature genetics, 34(3), 244, 2003) have confirmed that muscle mitochondrial respiratory metabolism was reduced by ageing or diabetes, thus resulting in coordinated changes in expression of genes involved in the oxidative phosphorylation process, and they have reported that PGC-1α is in charge of this change in gene expression. Mary et al (PNAS 100, 8466, 2003) have reported that decreased expression of PGC-1α is a main cause of insulin resistance and dysmetabolism in diabetic patients. Isabella et al (Am. J. Physiol. Cell Physiol. 284, c1669, 2003) have reported that PGC-1α is a key factor stimulating adaptation of mitochondria to changes in environment due to a thyroid hormone, T3, and muscle contraction. Kim et al (The Korean Journal of Biochemistry & Molecular Biology, 11, 16, 2004) have reported that through the causal relation between glucose/fatty acid metabolism, abnormalities in the amount and quality of mitochondria induces insulin resistance and furthermore, is a main cause of metabolic syndrome.

The present inventors carried out an extensive search for metabolism-activating drugs, based on the assumption that materials activating metabolism will be effective for treatment of metabolic syndrome diseases, and as a result, have confirmed that tanshinone derivatives are effective ingredients for therapeutic agents.

SUMMARY OF THE INVENTION

Therefore, the present invention has been made to solve the above problems, and technical problems that have been desired to be solved from the past.

The present inventors have conducted a variety of extensive and intensive study and experimentation. As a result of such extensive investigation, the inventors have found that tanshinone derivatives, extracted from Danshen (*Salvia miltiorrhiza*), have efficacy activating metabolism in cells and tissues, and further found that when ob/ob mice, a model of obesity caused by decreased secretion of leptin, db/db mice, a model of obesity/diabetes, and DIO (diet-induced obesity) mice, caused by high fat dietary conditions, are treated with tanshinone derivatives, these materials are effective for preventing and treating metabolic syndrome including obesity and diabetes mellitus. The present invention has been completed based on these findings.

Therefore, an object of the present invention is to provide a composition for preventing and treating metabolic syndrome, comprising, as an effective ingredient, tanshinone derivatives exhibiting prophylactic and therapeutic effects on such a metabolic syndrome through activation of metabolic activators, in myoblast C2C12 cells and adipocytes, and animal disease models.

DETAILED DESCRIPTION OF THE INVENTION

In accordance with an aspect of the present invention, the above and other objects can be accomplished by the provision of a composition for preventing or treating obesity and metabolic syndrome diseases, comprising a therapeutically and/or prophylactically effective amount of tanshinone derivatives from Danshen (*Salvia miltiorrhiza*) extact as an effective ingredient.

Physiological activities of tanshinone derivatives known hitherto are as follows. Toshiyuki et al (Planta Med. 2002. 68, 1103-1107) have reported that tanshinone VI attenuates hypertrophy of cardiac myocytes and inhibits synthesis of collagen by cardiac fibroblasts thereby retarding fibrosis of cardiac fibroblasts. Choi et al Planta Med. 2004, 70, 178-180) have suggested the possibility of using tanshinone derivatives as an anti-allergic agent by inhibition of mast cell degranulation. Ip et al (Planta Med. 2002, 68, 1077-1081) demonstrated the hepatoprotective effects of dihydroisotanshinone I against menadione-induced cytotoxicity in hepatocytes. Ren et al (Planta Med. 2004, 70, 201-204) have confirmed that tanshinone derivatives inhibit enzymatic activity of acetylcholinesterase. Kyoko et al (Biochemical Pharmacology, 64, 745-750 (2002)) have reported that tanshinone IIA sulfonate attenuates hypertrophy of cardiac myocytes induced by angiotensin II. Lee et al (Biosci. Biotechnol. Biochem. 63(12), 2236-2239, 1999) have reported that tanshinone derivatives generate superoxides and thus exhibit antibacterial activity. Kang et al (Immunopharmacology, 49, 355-361, 2000) have reported that tanshinone derivatives inhibit production of IL-12 and INF-γ in immunocytes. Ko et al (Arch. Pharm. Res. 25, 446-448, 2002) have reported that tanshinone derivatives inhibit enzymatic activity of DGAT. Zhou et al (Biochemical Pharmacology, 65, 51-57, 2003) have reported that tanshinone IIA sulfonate facilitates an electron-transfer reaction in mitochondria. Wang et al (Antimicrobial Agent & Chemotherapy, June, 1836-1841, 2003) have reported that tanshinone derivatives inhibit aminoglycoside-induced free radical formation. Yun et al (Korean Patent Publication Laid-open No. 2000-0027306) have asserted that tanshinone derivatives are effective as a therapeutic agent for treatment of hepatitis B. Sohn et al (Korean Patent Publication Laid-open No. 2004-0084482) disclose a therapeutic composition for hepatic fibrosis or hepatocirrhosis, containing tanshinone I as an effective ingredient. However, none of the above-mentioned publications and patents discloses or suggests prevention and treatment of obesity and metabolic syndrome diseases by enhancing activity of AMPK, as in the present invention.

The tanshinone derivatives, which are utilized as the effective ingredient in the composition of the present invention, are primarily present in Danshen, utilized as crude drug substance, such as *Salvia miltiorrhiza* and *Perovskia abrotanoides*. Tanshinone derivatives are broadly divided into tetrahydrophenanthrene derivatives and phenanthrene derivatives. Preferably, the composition in accordance with the present invention comprises one or more compounds selected from the group consisting of the above-mentioned derivatives and mixtures thereof.

Preferably, the tetrahydrophenanthrene derivative is one or more compounds selected from the group consisting of cryptotanshinone (Formula 1) and tanshinone IIA (Formula 2).

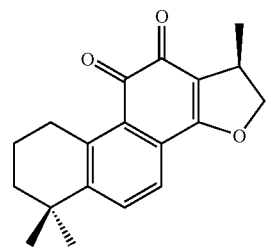

[Formula 1]

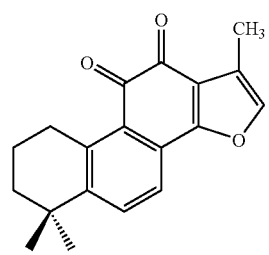

[Formula 2]

Preferably, the phenanthrene derivative is one or more compounds selected from the group consisting of tanshinone I (Formula 3) and 15,16-Dihydrotanshinone I (Formula 4).

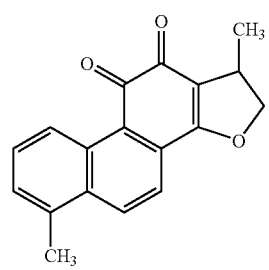

[Formula 3]

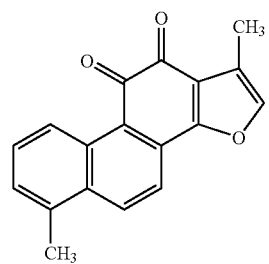

[Formula 4]

Tanshinone derivatives contained in Danshen (roots of *Salvia miltiorrhiza*) are composed of 0.29% tanshinone IIA, 0.23% cryptotanshinone, 0.11% tanshinone 1 and 0.054% 15,16-dihydrotanshinone I. As the main ingredient of Danshen, the tanshinone derivatives are diterpene o-quinone compounds. A biosynthesis process of these compounds is carried out by biosynthesis of cryptotanshinone from diterpene and biosynthesis of tanshinone derivatives of Danshen such as tanshinone IIA, 15,16-dihydrotanshinone I and tanshinone I, through oxidative processes such as demethylation or dehydrogenation of cryptotanshinone.

The present inventors have found that such tanshinone derivatives activate metabolism and thereby promote metabolism of glucose, proteins and lipid in the body and also inhibit fat accumulation in the body, thus being capable of treating metabolic syndrome. These finding and facts can also be demonstrated through the following examples. Specifically, the present inventors have measured the influence of tanshinone derivatives on activity of metabolic activators and expression of proteins and genes in myoblast cells (C2C12), and suppression of cellular differentiation of preadipocytes (3T3-L1 and F442A cells) and as a result, have confirmed that such compounds exhibit excellent metabolic activation. As can be seen through the effects of tanshinone derivatives on protein and gene expression, such tanshinone compounds may exhibit superior activity on metabolic activation, alone or in any combination thereof. Simultaneously, the present inventors have confirmed that inhibition of fatty acid synthesis, facilitation of fat acid oxidation and expression level of mitochondrial biogenesis factors correlate with structures of tanshinone derivatives.

Therefore, the composition in accordance with the present invention is comprised of one or more tanshinone derivatives selected from the group consisting of cryptotanshinone, tanshinone IIA, tanshinone 1 and 15,16-dihydrotanshinone I.

Such a composition includes all the cases as follows:

(i) Composition containing cryptotanshinone as the main ingredient;

(ii) Composition containing tanshinone IIA as the main ingredient, (iii) Composition containing tanshinone I as the main ingredient;

(iv) Composition containing 15,16-dihydrotanshinone I as the main ingredient, (v) Composition containing cryptotanshinone as the essential ingredient, and optionally, containing one or more compounds selected from the group consisting of tanshinone IIA, tanshinone 1 and 15,16-dihydrotanshinone I;

(vi) Composition containing tanshinone IIA as the essential ingredient, and optionally, containing one or more compounds selected from the group consisting of cryptotanshinone, tanshinone 1 and 15,16-dihydrotanshinone I;

(vii) Composition containing tanshinone I as the essential ingredient, and optionally, containing one or more compounds selected from the group consisting of cryptotanshinone, tanshinone IIA and 15,16-dihydrotanshinone I; and (vii) Composition containing 15,16-dihydrotanshinone I as the essential ingredient, and optionally, containing one or more compounds selected from the group consisting of cryptotanshinone, tanshinone IIA and tanshinone I.

If desired, the above-mentioned compositions may further comprise one or more tanshinone derivatives selected from the group consisting of 1β-hydroxycryptotanshinone, 1-oxocryptotanshinone, tanshinol B, tanshinol IIB, przewaquinone A, dihydroisotanshinone I, tanshinone IIA sulfonate, 1,2-dihydrotanshinone I and tanshinone VI.

More surprisingly, the present inventors have confirmed that enhancement effects of cryptotanshinone, tanshinone IIA, tanshinone 1 and 15,16-dihydrotanshinone I on AMPK activity is significantly increased by combinational use of two or more of these compounds. Such a significantly synergistic effect was not totally predicted and it was also confirmed that such effect was exhibited, regardless of kinds of those four tanshinone derivatives. Therefore, among combinations of the above-mentioned compositions, compositions (v) through (viii) are particularly preferred.

As specific examples of compositions (v) through (viii), mention may be made of the following:

Composition comprising cryptotanshinone and 15,16-dihydrotanshinone I;

Composition comprising cryptotanshinone and tanshinone IIA;

Composition comprising tanshinone IIA and 15,16-dihydrotanshinone I;

Composition comprising tanshinone IIA and tanshinone I,

Composition comprising 15,16-dihydrotanshinone I and tanshinone I; and

Composition comprising tanshinone I and cryptotanshinone.

In the compositions as mentioned above, the ratio between the two ingredients is preferably in the range of 10:1 to 1:10 (w/w), and more preferably in the range of 5:1 to 1:5.

The composition of tanshinone derivatives contained in naturally occurring Danshen may exhibit different distributions depending upon the harvesting season or cultivation region. Considering the above-mentioned synergistic effects, it is necessary to have the optimal composition ratio between tanshinone derivatives so as to exert efficacy thereof uniformly. The present inventors have confirmed effects of tanshinone derivatives on expression activity of genes and proteins and characteristics according to structural differences therebetween. By optionally controlling the composition ratio on the basis of these results, the present inventors confirmed effects of adjusting the ratio between tanshinone derivatives on decrease of body weight and then attempted to obtain the optimal composition ratio.

As described above, when the composition in accordance with the present invention comprise one or more compounds selected from the group consisting of tetrahydrophenanthrene derivatives and phenanthrene derivatives, and preferably comprises both derivatives, the preferred combination ratio therebetween may be in the range of 10:1 to 1:10 (by weight), more preferably in the range of 5:1 to 1:5, and particularly preferably in the range of 2.5:1 to 1:2.5. Preferably, the tetrahydrophenanthrene derivative component contains both cryptotanshinone and tanshinone IIA, and the ratio therebetween is in the range of 5:1 to 1:5. In addition, the phenanthrene derivative component contains both 15,16-dihydrotanshinone I and tanshinone I, and the ratio therebetween is in the range of 5:1 to 1:5.

The present inventors have further confirmed that tanshinone derivatives have very superior prophylactic and therapeutic effects of metabolic syndrome, through extensive in vivo metabolic syndrome-prophylactic and therapeutic experiments in the ob/ob mice, a model of obesity, the db/db mice, a model of obesity/diabetes, and the DIO (diet-induced obesity) mice caused by high fat diet.

As a result, the composition for preventing and treating metabolic syndrome comprising tanshinone derivatives as the effective ingredient can prevent and treat metabolic syndrome through activation of metabolism, and thus it is predicted that they can be developed as various therapeutic agents for a variety of diseases associated with metabolic syndrome. The composition for preventing and treating metabolic syndrome in accordance with the present invention comprises the above tanshinone derivatives or an optional mixture thereof as the effective ingredient, and can be formulated into the metabolic syndrome-prophylactic and therapeutic agent, in conjunction with a pharmaceutically acceptable carrier, if necessary.

1. Pharmacological Properties

The composition in accordance with the present invention is useful for prophylaxis and/or treatment of clinical conditions associated with metabolic syndrome. These clinical conditions include, but are not limited to, common obesity, abdominal obesity, hypertension, arteriosclerosis, hyperinsulinemia, hyperglycemia, type II diabetes mellitus and dyslipidemia characteristically appearing with insulin resistance. Dyslipidemia, also known as the atherogenic lipoprotein profile of phenotype B, is characterized by significantly elevated non-esterified fatty acids, elevated very low density lipoproteins (VLDL) triglyceride rich particles, high values of ApoB, the presence of small, dense, low density lipoprotein (LDL) particles, high values of ApoB in the presence of phenotype B, and low value of high density lipoproteins (HDL) associated with low value of ApoAI particles.

The composition in accordance with the present invention is expected to be useful for treating patients suffering from combined or mixed dyslipidemia, or hypertriglycerimia having or having not other signs of metabolic syndrome and suffering from various degrees of dyslipidemia after meals.

The composition in accordance with the present invention is expected to have anti-inflammatory properties and also to lower the cardiovascular morbidity and mortality associated with arteriosclerosis due to dyslipidemia. These cardiovascular disease conditions include macro-angiopathies of various internal organs causing myocardial infarction, cardiac insufficiency, cerebrovascular disease and peripheral arterial insufficiency of the lower extremities. Because of their insulin sensitizing effects, the composition of the present invention is also expected to prevent or retard the progress of type II diabetes mellitus in metabolic syndrome and development of diabetes during pregnancy. Therefore, the composition of the present invention is also expected to retard the progress of chronic complications associated with clinical hyperglycaemia in diabetes, for example, the micro-angiopathies causing renal disease, retinal damage and peripheral vascular diseases of the lower extremities. Furthermore, the composition of the present invention may be useful in treatment of various conditions other than the cardiovascular system, regardless of association with insulin resistance, for example polycystic ovarian syndrome, obesity, cancers, inflammatory diseases, and neurodegenerative diseases such as Mild Cognitive Impairment (MCI), Alzheimer's disease, Parkinson's disease and multiple sclerosis.

The composition of the present invention exhibits inhibitory effects against development of fatty liver (hepatic steatosis) in the liver and also activates β-oxidation of fatty acids, thereby playing a role in lowering concentration of triglycerol and thus is expected to be useful for preventing or treating fatty liver and hepatitis due to lipid dysmetabolism of alcoholic and non-alcoholic liver.

The composition of the present invention varies lipid composition in various tissues. In addition, it can vary fat content and distribution and also reduce plasma cholesterol and triacylglycerol levels.

The composition of the present invention is effective for formation of NO in endothelial cells and thus is expected to be useful for preventing or treating cardiac diseases, vascular diseases, hypertension and erectile dysfunction. As hypertension-causing diseases, mention may be made of cardiac insufficiency, myocardial infarction, rupture of the cerebrovascular system, thrombosis and kidney damage.

The composition of the present invention is a material eliciting promotion of fatty acid oxidation and energy consumption in distal tissues and thereby is expected to be useful for treating or preventing common obesity and also in removing localized fat deposits such as subcutaneous and abdominal fat. Accordingly, the composition of the present invention is expected to be useful for delivering drugs in the form of ointments, patches including anti-inflammatory patches, and creams when desired to remove fat from particular regions where fat is locally deposited, such as removing subcutaneous fat from protuberant parts of the eye-lids, arms and hips, abdominal fat and fat of particular regions, for example, cellulite.

Further, the composition of the present invention may be used as an anti-diabetic agent by lowering the level of blood glucose. In addition, it was confirmed that the composition of the present invention improves decreased sensitivity to insulin and thereby enhances the effects of insulin.

The composition of the present invention promotes mitochondrial biogenesis, thereby increasing active capacity of mitochondria and at the same time, induces conversion of muscle tissues into motor tissues, thereby resulting in improved locomotive capacity of patients, reinforced endurance, improved energy productivity, fatigue-recovery, increased vital power, reduction of oxidative stress through increased ability to remove reactive oxygen species (ROS) and free radicals, and therefore the composition is expected to be effective for treating diseases concerned.

As diseases that may be caused by reactive oxygen species (ROS), mention may be made of the following: arteriosclerosis, diabetes mellitus, neurological diseases, kidney diseases, hepatocirrhosis, arthritis, Retinopathy of Prematurity, ocular uveitis, senile cataract, side effect disorders by radiotherapy, bronchial damage due to smoking, side effect disorders by carcinostatic agents, cerebral edema, lung edema, foot edema, cerebral infarction, hemolytic anemia, progeria, epilepsy, Alzheimer's disease, Down's syndrome, Crohn's disease and collagen disease.

As mentioned above, the composition of the present invention was shown to provide beneficial effects for all of the above-mentioned conditions and diseases, by modulating glucose and lipid homeostasis. Therefore, it can be seen that the composition of the present invention is a suitable material for control of metabolic syndrome.

The present invention relates to use of a compound for preparing a pharmaceutical composition for therapy and/or prophylaxis of multiple metabolic syndrome (metabolic syndrome), that is, metabolic syndrome characteristically appearing with hyperinsulinemia, insulin resistance, obesity, glucose intolerance, type II diabetes mellitus, dyslipidemia, cardiovascular diseases or hypertension, in particular.

2. Pharmaceutical Preparations

The compositions for preventing and treating metabolic syndrome comprising tanshinone derivatives as the effective ingredient can prevent and treat metabolic syndrome through activation of metabolism, and thus it is believed that they can be developed as various drugs for a variety of diseases associated with metabolic syndrome. The composition for preventing and treating metabolic syndrome in accordance with the present invention comprises the above-mentioned tanshinone derivatives as the effective ingredient, and can be formulated into the metabolic syndrome-prophylactic and therapeutic agent, in conjunction with a pharmaceutically acceptable carrier, if necessary.

A suitable dose of the pharmaceutical composition of the present invention may vary depending upon various factors such as formulation method, administration fashion, age, weight and sex of patients, pathological conditions, diet, administration time, administration route, excretion rate and sensitivity to response. The pharmaceutical composition of metabolic syndrome-prophylactic and therapeutic agent in accordance with the present invention comprises tanshinone derivatives as the effective ingredient. The tanshinone derivatives can be administered via oral or parenteral routes upon clinical administration and can be used in general forms of pharmaceutical formulations. That is, the composition in accordance with the present invention may be administered by various oral and parenteral formulations, upon practical clinical administration. When formulating, the formulations are prepared using conventional filling agents, extenders, binding agents, wetting agents, disintegrating agents, diluents such as surfactants, or excipients. Solid formulations for oral administration include, for example, tablets, pills, powders, granules and capsules, and are prepared by mixing tanshinone derivatives with one or more excipients, such as starch, calcium carbonate, sucrose, lactose and gelatin. Lubricating agents such as magnesium stearate and talc may also be used, except for simple excipients. As liquid formulations for oral administration, mention may be made of suspensions, solutions for internal use, emulsions and syrups. In addition to generally used simple diluents such as water and liquid paraffin, the above-mentioned formulations can contain various excipients, for example wetting agents, sweetening agents, aromatics and preservatives. Formulations for parenteral administration include sterilized aqueous solutions, non-aqueous solvents, suspensions, emulsions, lyophilized formulations and suppositories. As non-aqueous solvents and suspensions, there may be used propylene glycol, polyethylene glycol, vegetable oil such as olive oil, injectable ester such as ethylolate, etc. As base materials for suppositories, Witepsol, macrogol, Tween 61, cacao butter, laurin butter, glycerol and gelatin may be used.

Dosage units may contain one-, two-, three- or four-fold amount of individual dose, or ½, ⅓ or ¼ fold amount of individual dose. Preferably, an individual dose contains an amount of the effective drug that is administered one time, and typically corresponds to the total amount administered for one day, or ½, ⅓ or ¼ fold-amount thereof. Although effective doses of tanshinone derivatives are concentration-dependent, they are preferably in the range of 0.1 to 1,000 mg/kg, more preferably 0.4 to 500 mg/kg and may be administered 1 to 6 times a day. Therefore, tanshinone derivatives may be administered in the range of 0.1 to 6,000 mg/day/kg bw, for adults.

In accordance with another aspect of the present invention, there is provided a health and functional food composition for preventing and treating metabolic syndrome, containing tanshinone derivatives as an effective ingredient.

The term "a health and functional food" used throughout the specification of the present invention refers to a food in which tanshinone derivatives are added to general foods to improve functions thereof. Tanshinone derivatives may be added to general foods or may be prepared in the form of capsules, powders, suspensions and the like. Intake of such a health and functional food containing tanshinone derivatives provides beneficial effects for health, and exhibits advantages in that there are no side effects caused by prolonged use of drugs because food material is used as the raw material, unlike conventional drugs.

If it is desired to use tanshinone derivatives of the present invention as a food additive, these derivatives can be added alone, or can be used in conjunction with other food or food ingredients, or may be used appropriately according to other conventional methods. Mixed amount of effective ingredients may be suitably determined depending upon the purpose of use (prophylactic, health or therapeutic treatment). Generally, in producing foods or beverages with which tanshinone derivatives are mixed, these derivatives may be added in an amount of 0.0001 to 10% by weight, and preferably in an amount of 0.1 to 5% by weight, relative to the total weight of raw materials. However, when prolonged intake is intended for the purpose of health and hygiene or for health control, the above-mentioned amount of tanshinone derivatives may be adjusted below the above-mentioned range. In addition, the health food of the present invention preferably contains tanshinone derivatives falling within the determined toxicity range, when it is employed as a pharmaceutical composition.

There is no particular limit to kinds of the above-mentioned foods. As examples of foods to which the tanshinone derivatives can be added, mention may be made of meats, sausages, bread, chocolate, candies, snack, confectionary, pizza, Ramen, other noodles, gum, skimmed milk, dried foods, raw foods, dairy products including lactic acid bacteria-fermented milk and ice cream, various soups, beverages, teas, drinks, alcoholic beverages and multi-vitamin preparations. Specifically, as examples of health foods containing tanshinone derivatives, mention may be made of health foods and special favorite products such as squeezed liquid, tea, jelly and juice made of tanshinone derivatives as main ingredients. In addition, mention may be made of folk medicines for edema, nephritis and urethritis as targets.

When it is desired to use tanshinone derivatives of the present invention as cosmetic raw materials, these derivatives can be added by themselves or can be used in conjunction with other cosmetic ingredients, or may be used appropriately according to other conventional methods. Mixed amount of effective ingredients may be suitably determined depending upon the purpose of use thereof. Generally, in producing cosmetics using tanshinone derivatives, these derivatives may be added in an amount of 0.0001 to 10% by weight, and preferably in the amount of 0.1 to 5% by weight, relative to the total weight of raw materials. Cosmetics include, but are not limited to, aftershaves, lotions, creams, packs and color cosmetics.

Tanshinone derivatives in accordance with the present invention may be extracted using Danshen (*Salvia miltiorrhiza*) as dried drug material or raw drug material, or may be synthesized by organochemical methods.

A process for extracting tanshinone derivatives from Danshen comprises: a) subjecting Danshen to water or organic solvent extraction to obtain crude extracts, b) filtering the crude extracts, followed by (vacuum) concentration, and c) optionally, removing solvent.

For example, Danshen is extracted with methanol, vacuum concentrated and then re-extracted with methylene chloride to obtain a concentrated solution. The solution is purified via silica column chromatography to obtain pure tanshinone derivatives. The present invention will be described in more detail by way of the following examples.

DETAILED DESCRIPTION OF THE DRAWINGS

The above and other objects, features and other advantages of the present invention will be more clearly understood from the following detailed description taken in conjunction with the accompanying drawings, in which.

Figure 3:
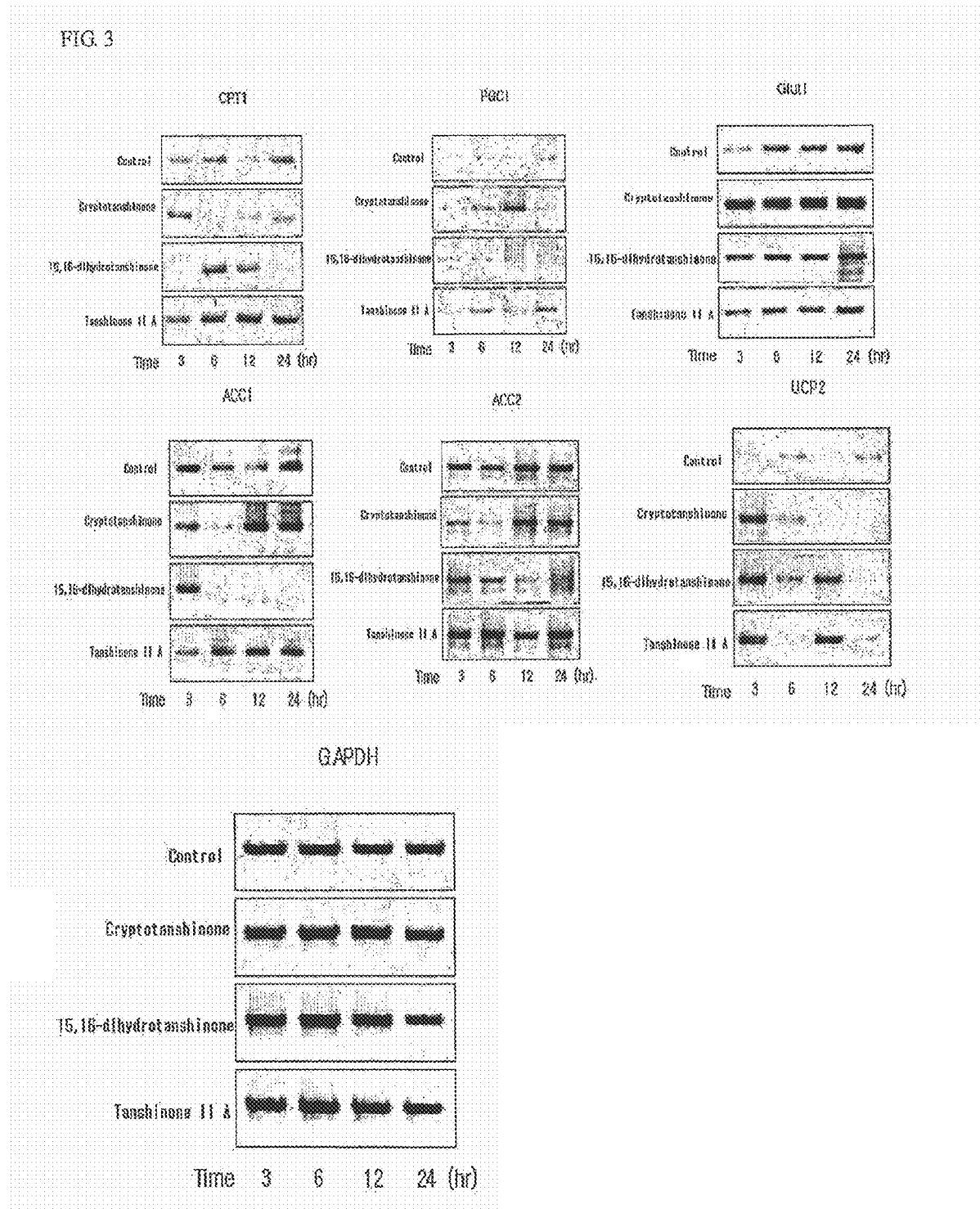
Figure 4:
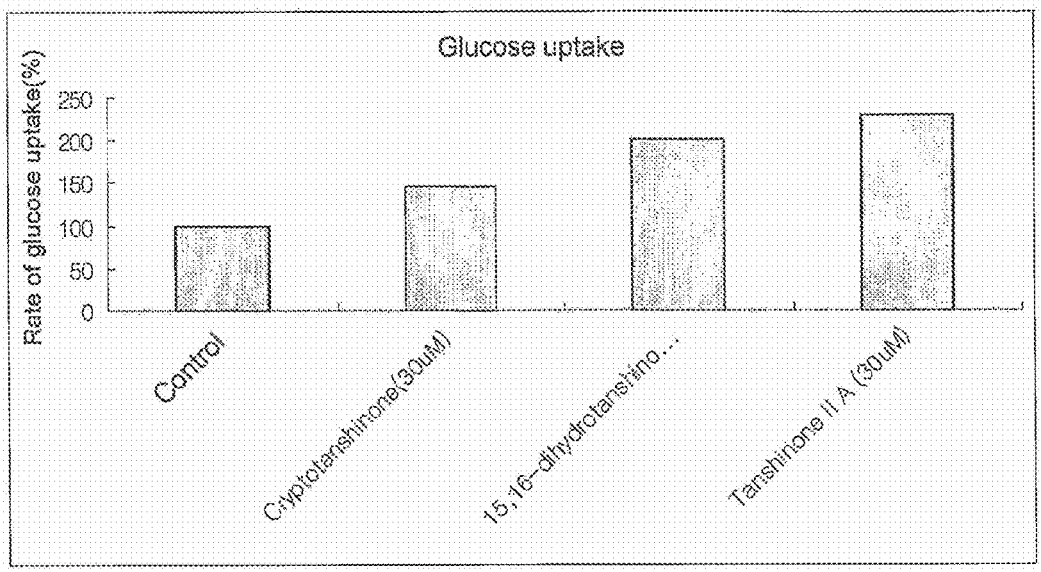
Figure 5:
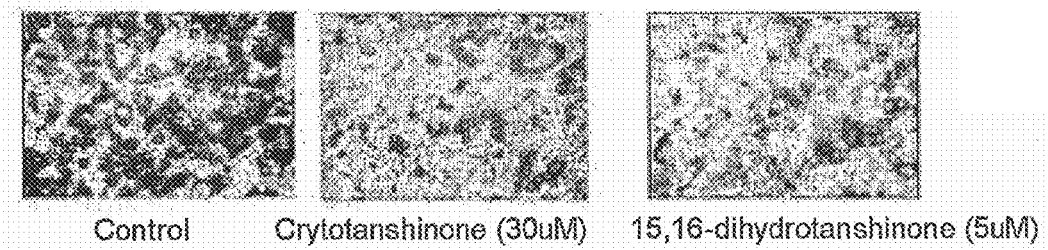
Figure 8:
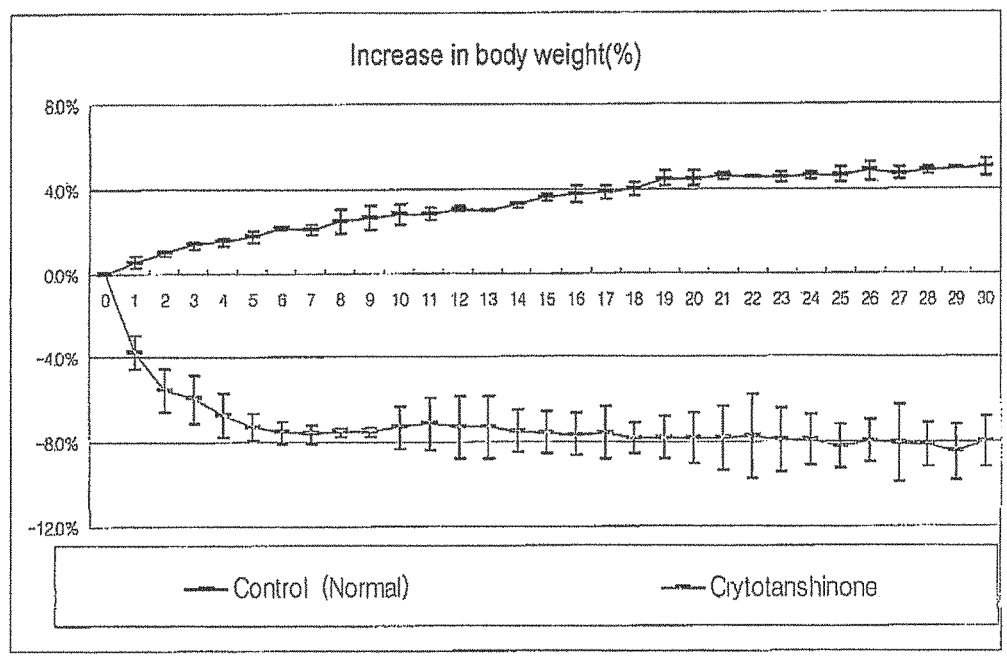
Figures 9, 10:
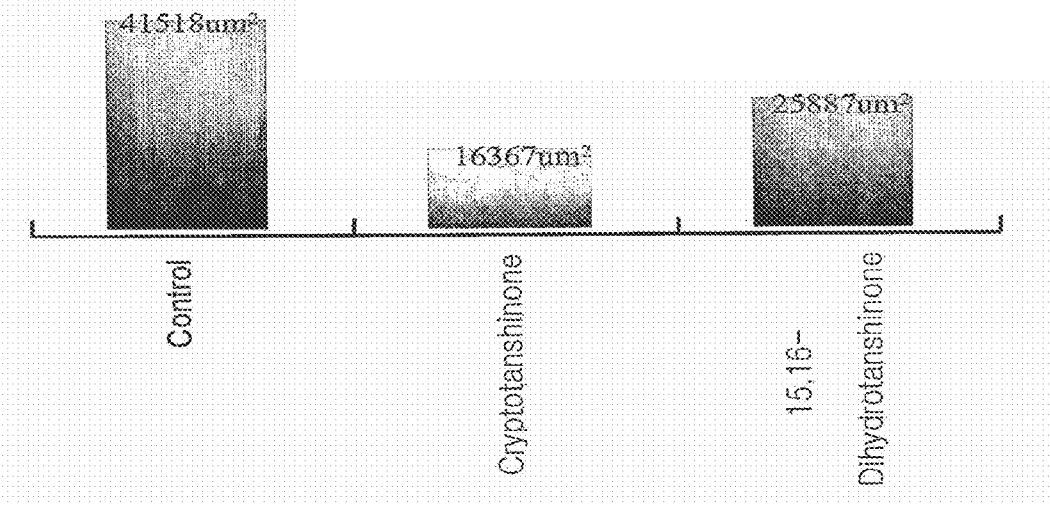
Figure 11:
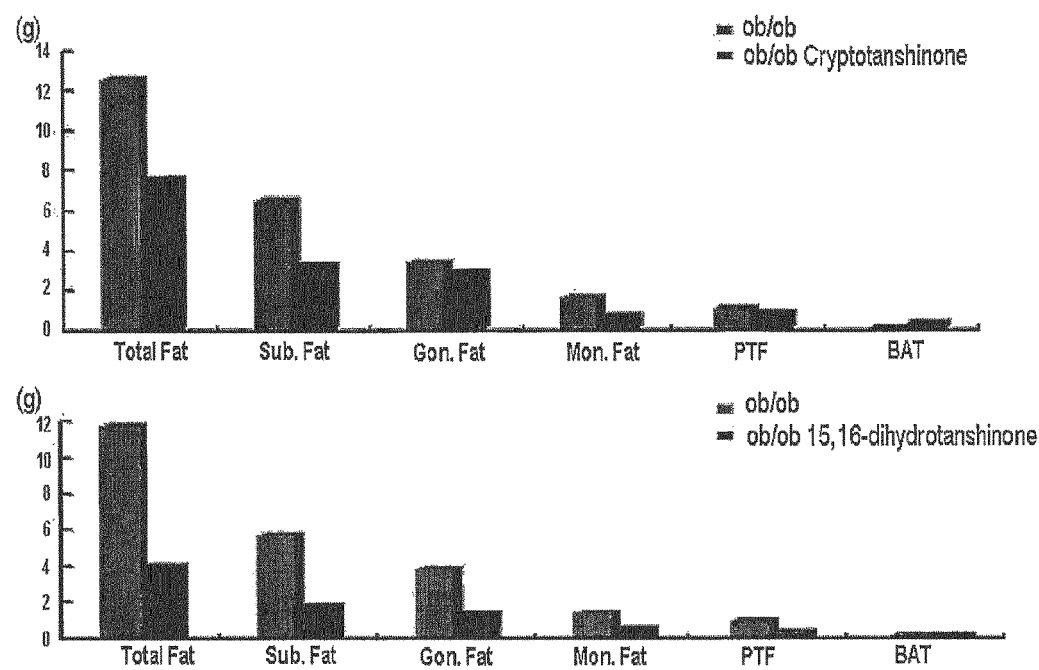
Figures 12, 13:
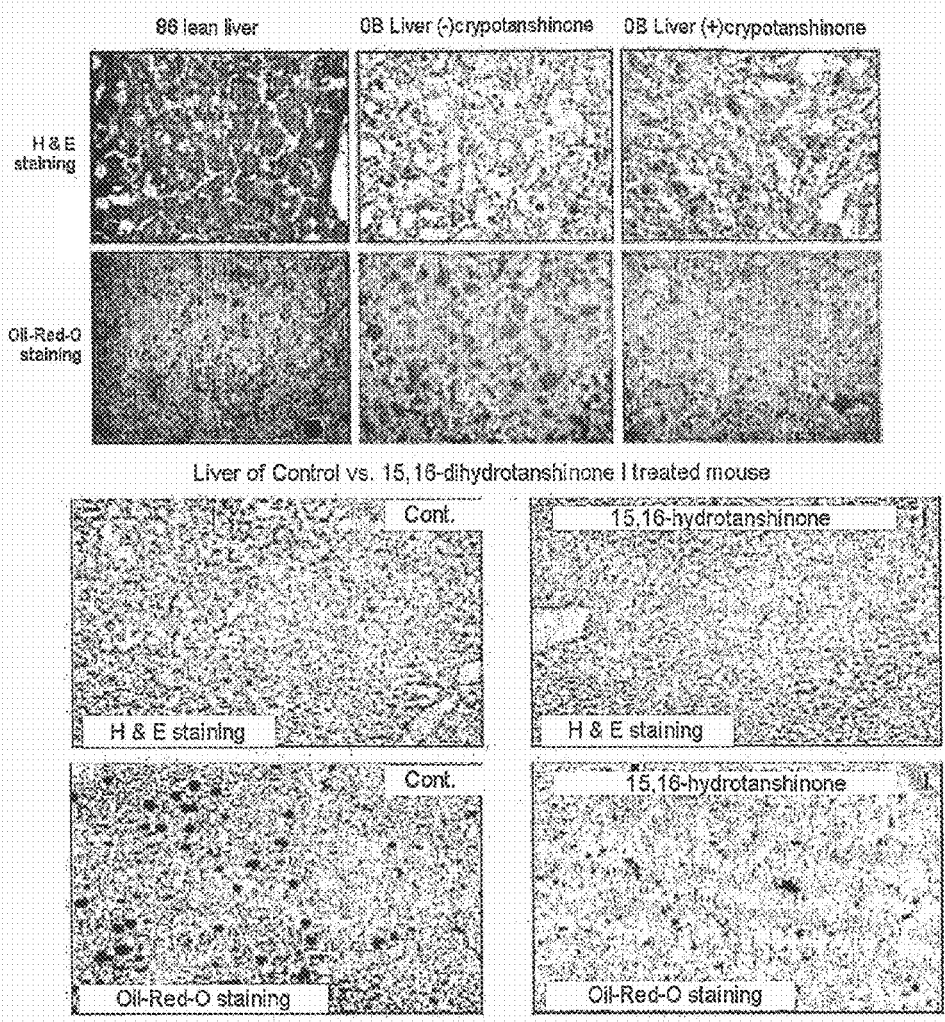
Figures 14, 15:
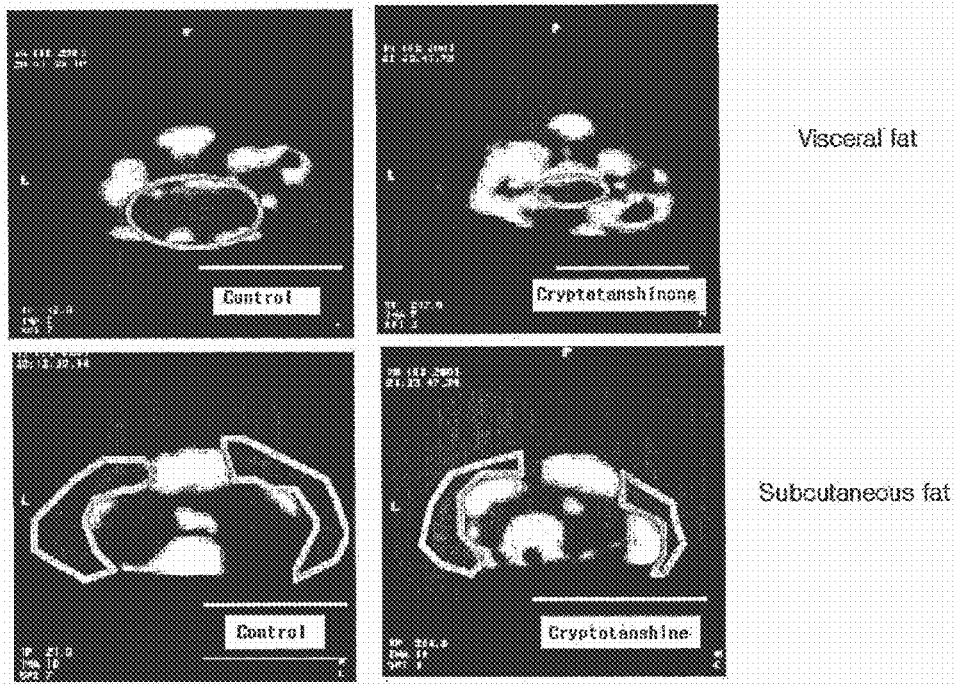

FIG. 3 shows results of Western blotting to determine effects of tanshinone derivatives on gene expression of ACC 1 and 2, UCP-2, CPT1, PGC-1α and GLUT1, after treatment of myoblast cell line C2C12 with tanshinone derivatives, FIG. 4 is a graph comparing effects of tanshinone derivatives on cellular glucose uptake, between the treatment group and control group, after treatment of myoblast cell line C2C12 with tanshinone derivatives;

FIG. 5 is a micrograph showing results of effects of tanshinone derivatives on adipocyte differentiation, after treatment of preadipocyte cell line F442A with tanshinone derivatives, FIG. 6 is a graph comparing results between the treatment group and control group in effects of tanshinone derivative on insulin sensitivity, after treatment of myoblast cell line C2C12 with tanshinone derivatives;

FIG. 7 shows results of effects of cryptotanshinone on changes in body weight over time, after treatment of an animal model of obesity, DIO (diet-induced obesity) mice, with cryptotanshinene;

FIGS. 8 and 9 are, respectively, a graph and table showing effects of tanshinone derivatives on changes in body weight over time, after treatment of an animal model of obesity, C57BL/6JL Lep ob/Lep ob mice, with tanshinone derivatives;

FIG. 10 is a graph comparing changes in adipocyte size between the treatment group and control group, after treatment of an animal model of obesity, C57BL/6JL Lep ob/Lep ob mice, with tanshinone derivatives;

FIG. 11 is a graph comparing fat distribution in terms of numerical values for respective organs between the treatment group and control group, after treatment of an animal model of obesity, C57BL/6JL Lep ob/Lep ob mice, with tanshinone derivatives;

FIG. 12 is a graph comparing adipose tissue distribution and fat accumulation in the livers between the treatment group and control group, by way of staining of livers following treatment of an animal model of obesity, C57BL/6JL Lep ob/Lep ob mice, with tanshinone derivatives;

FIG. 13 is a table comparing changes in lipid and antioxidation indicator materials in liver tissues between the treatment group and control group, after treatment of an animal model of obesity, C57BL/6JL Lep ob/Lep ob mice, with tanshinone derivatives;

FIG. 14 is a table comparing changes in blood lipid and glucose between the treatment group and control group, after treatment of an animal model of obesity, C57BL/6JL Lep ob/Lep ob mice, with tanshinone derivatives;

FIG. 15 is a micrograph comparing changes in visceral fat distribution of nice between the treatment group and control group, after treatment of an animal model of obesity, C57BL/6JL Lep ob/Lep ob mice, with tanshinone derivatives, FIG. 16 is a table showing effects of tanshinone derivatives on changes in blood glucose, after treatment of an animal model of obesity, Lepr db/Lepr db mice, with tanshinone derivatives;

FIG. 17 is a table comparing activity of compositions by double combination of tanshinone derivatives in accordance with the present invention;

FIG. 18 is a table showing changes in activity with respect to changes of ingredient ratio in compositions of the present invention;

FIG. 19 is a table comparing AMPK activity of compositions by triple combination of tanshinone derivatives in accordance with the present invention; and FIG. 20 is a table showing results of effects of combination ratio between tetrahydrophenanthrene derivative group and phenanthrene derivative group of tanshinone derivatives on changes in body weight, after treatment of an animal model of obesity, C57BL/6JL Lep ob/Lep ob mice, at various combination ratios.

EXAMPLES

Now, the present invention will be described in more detail with reference to the following Examples. These examples are provided only for illustrating the present invention and should not be construed as limiting the scope and sprit of the present invention.

Example 1

Isolation of Tanshinone Derivatives 5 kg of Danshen (*Salvia miltiorrhiza*) material was purchased from a Chinese medicinal herb shop and other necessary materials were collected in fields and mountains or were purchased from the shop. Danshen was eluted with 50 L of methanol for 24 hours and concentrated under reduced pressure. 1500 mL of water was added to the resulting material. Then, an equal amount of n-hexane, dichloromethane ($CH_2Cl_2$) and ethyl acetate (EtOAc) were added and sequentially extracted two times so as to obtain a gelatinous red extract. When activity was examined on the respective layers thus obtained, the activity was highest in the dichloromethane layer.

Silica gel (Kieselgel 60, 230 to 460 mesh, Merck) was sufficiently swelled with 100% n-hexane and then packed into a column (530 cm high). 50 g of the extract obtained from the $CH_2Cl_2$ layer was dissolved in a trace amount of EtOAc and n-hexane and the resulting sample was loaded onto the column. After loading and sufficiently eluting the sample, the resulting eluate was eluted with EtOAc gradient of from 10 to 20%, and was sequentially eluted with $MeOH/CHCl_3$ gradient of 0/100 (v/v)→50/50 (v/v) to obtain tanshinone derivatives. Through measurement of AMPK activity, active fractions were pooled and concentrated under reduced pressure.

The material, which exhibited activity in the first column, was again separated using silica gel (Kieselgel 60, 230 to 460 mesh, Merck). This was followed by swelling with 100% n-hexane and packing into a column (425 cm high). EtOAc/n-hexane=0/100 (v/v)→20/80 (v/v) was used as a developing solvent. Fractions exhibiting inhibitory activity were pooled and concentrated under reduced pressure.

Next, Prep-TLC was carried out under the developing solvent, EtOAc/n-hexane=30/70 (v/v). TLC was carried out in each step and the degree of separation of the respective fractions was observed. As the developing solvent, EtOAc/n-hexane=80/20 (v/v) was used in a normal phase. Search for the respective materials was performed by heating and developing a TLC plate in a hot plate using an anisaldehyde staining solvent (5% $H_2SO_4$, 2.5% acetic acid, 5% anisaldehyde, and 87.5% ethanol). In this manner, tanshinone derivatives were extracted, separated and purified.

Example 2

Structural Analysis of Separated Active Material

NMR analysis was performed to determine structures of cryptotanshinone, tanshinone I, tanshinone IIA and 15,16-dihydrotanshinone I separated in Example 1, respectively.

Cryptotanshinone

1H-NMR ($CDCl_3$): δ 7.42 (2H, ABq, J=8.0 Hz), 4.83 (1H, t, J=9.2 Hz), 4.31 (1H, dd, J=9.2 and 6.0 Hz), 3.55 (1H, m), 3.17 (2H, br t), 1.65 (4H, m), 1.40 (3H, d, J=6.8 Hz), 1.28 (6H, s)

13C-NMR ($CDCl_3$): δ 9.58 (C-1), 19.00 (C-2), 37.73 (C-3), 34.76 (C-4), 143.57 (C-5), 132.48 (C-6), 122.43 (C-7), 128.30 (C-8), 126.19 (C-9), 152.28 (C-10), 184.116 (C-11), 175.59 (C-12), 118.21 (C-13), 170.66 (C-14), 81.38 (C-15), 34.54 (C-16), 18.74 (C-17), 31.85 (C-18), 31.80 (C-19)

Tanshinone II-A

1H-NMR (CDCl$_3$, 300.40 MHz) δ 7.63 (1H, d, J=8.2 Hz), 7.54 (1H, d, J=8.2 Hz), 7.22 (1H, s), 3.18 (2H, t, J=6.6 Hz), 2.26 (3H, s), 1.78 (2H, m), 1.65 (2H, m), 1.31 (6H, s).

13C-NMR (CDCl$_3$, 75.45 MHz) δ 184.29, 176.43, 162.38, 150.80, 145.14, 141.96, 134.13, 128.12, 127.16, 121.81, 120.91, 120.57, 38.52, 35.33, 32.51, 30.56, 19.79, 9.46.

15, 16-Dihydrotanshinone I

1H-NMR (CDCl$_3$, 300.40 MHz) δ 9.24 (1H, d, J=10.6 Hz), 8.24 (1H, d, J=10.3 Hz), 7.69 (1H, d, J=10.3 Hz), 7.54 (1H, dd, J=10.6, 8.4 Hz), 7.41 (1H, d, J=8.4 Hz), 4.95 (1H, t, J=11.3 Hz), 4.41 (1H, dd, J=11.3 Hz, 7.5 Hz, 3.62 (1H, m), 2.66 (3H, s), 1.38 (3H, d, J=8.1 Hz).

13C-NMR (CDCl$_3$, 75.45 MHz) δ 184.26, 175.67, 170.56, 142.00, 134.95, 134.72, 132.06, 131.90, 130.38, 128.81, 128.18, 126.01, 124.99, 120.28, 118.32, 114.06, 81.62, 34.68, 19.85, 18.81.

Tanshinone I

1H-NMR (CDCl$_3$, 300.40 MHz) δ 9.19 (1H, d, J=10.6 Hz), 8.23 (1H, d, J=10.3 Hz), 7.73 (1H, d, J=10.3 Hz), 7.50 (1H, dd, J=10.6, 8.5 Hz), 7.30 (1H, d, J=8.5 Hz), 7.26 (1H, q, J=1.3H), 2.64 (3H, s), 2.25 (3H, d, J=1.3 Hz).

13C-NMR (CDCl$_3$, 75.45 MHz) δ 183.38, 175.55, 161.13, 142.00, 135.18, 133.58, 132.90, 132.69, 130.63, 129.57, 128.31, 124.73, 123.03, 121.72, 120.43, 118.69, 19.84, 8.79.

Example 3

Determination of AMPK Activity

Myoblast cells, C2C12, were cell cultured in DMEM containing 10% bovine calf serum. When cell density reached a range of about 85% to 90%, the culture medium was replaced with 1% bovine calf serum medium to induce differentiation of cells. Enzymatic activity of AMPK was determined as follows. C2C12 cells were lysed to obtain protein extracts and then ammonium sulfate was added to a final concentration of 30%, followed by precipitation of proteins. Protein precipitates were dissolved in a buffer (62.5 mM Hepes, pH 7.2, 62.5 mM NaCl, 62.5 mM NaF, 1.25 mM Na pyrophosphate, 1.25 mM EDTA, 1 mM DTT, 0.1 mM PMSF, and 200 μM AMP). Thereafter, 200 μM SAMS peptide MRSAMSGLHLVKRR: the underlined serine residue is a phosphorylation site, as an AMPK phosphorylation site of acetyl-CoA carboxylase) and [γ-32P]ATP were added thereto and reactants were reacted for 10 minutes at 30° C. This was followed by spotting of the resulting reaction solution on p81 phosphocellulose paper. The p81 paper was washed with a 3% phosphate solution and radioactivity was measured. For each reaction condition, reactions involving no SAMS peptide were also conducted and basic values were subtracted from the total values.

Figure 1:
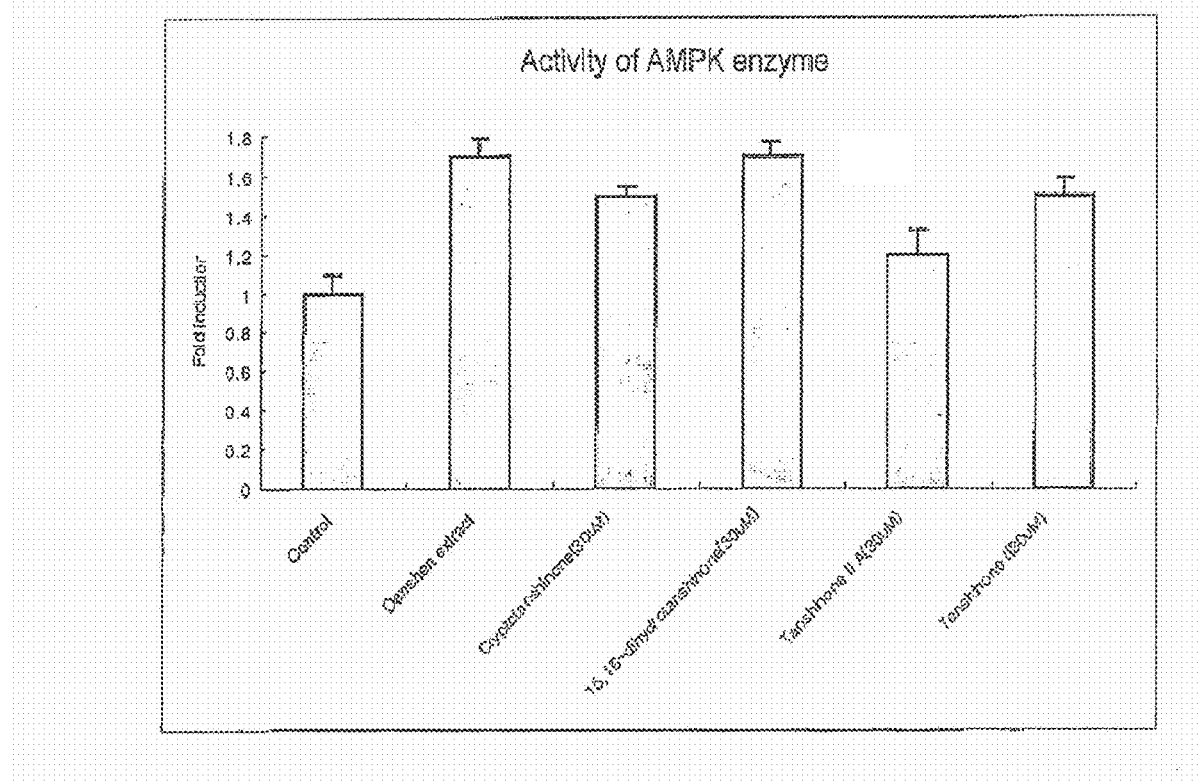
FIG. 1 is a bar graph comparing activity of AMPK (AMP-activated protein kinase) between the treatment group and control group, after treatment of myoblast cell line C2C12 with Danshen (*Salvia miltiorrhiza*) extract and tanshinone derivatives.

As can be seen from FIG. 1, when myoblast cells, C2C12, were treated with Danshen extracts and tanshinone derivatives, this leads to increased enzymatic activity of AMPK.

Example 4

Determination of Expression Levels of t-AMPK p-AMPK, p-ACC and GLUT 4 Enzymes

Myoblast cells, C2C12 were cell cultured in DMEM containing 10% bovine calf serum. When cell density reached a range of about 85% to 90%, the culture medium was replaced with 1% bovine calf serum medium to induce cellular differentiation. Differentiated cells were treated with 30 μM tanshinone derivatives, respectively. Enzymatic activity of AMPK was measured by lysing C2C12 cells to obtain protein extracts and subjecting protein extracts to Western Blot analysis so as to determine the amount of total AMPK, p-AMPK (phosphorylated AMPK), p-ACC (phosphorylated acetyl-CoA carboxylase) and GLUT4 (glucose transporter 4) proteins.

Figure 2:
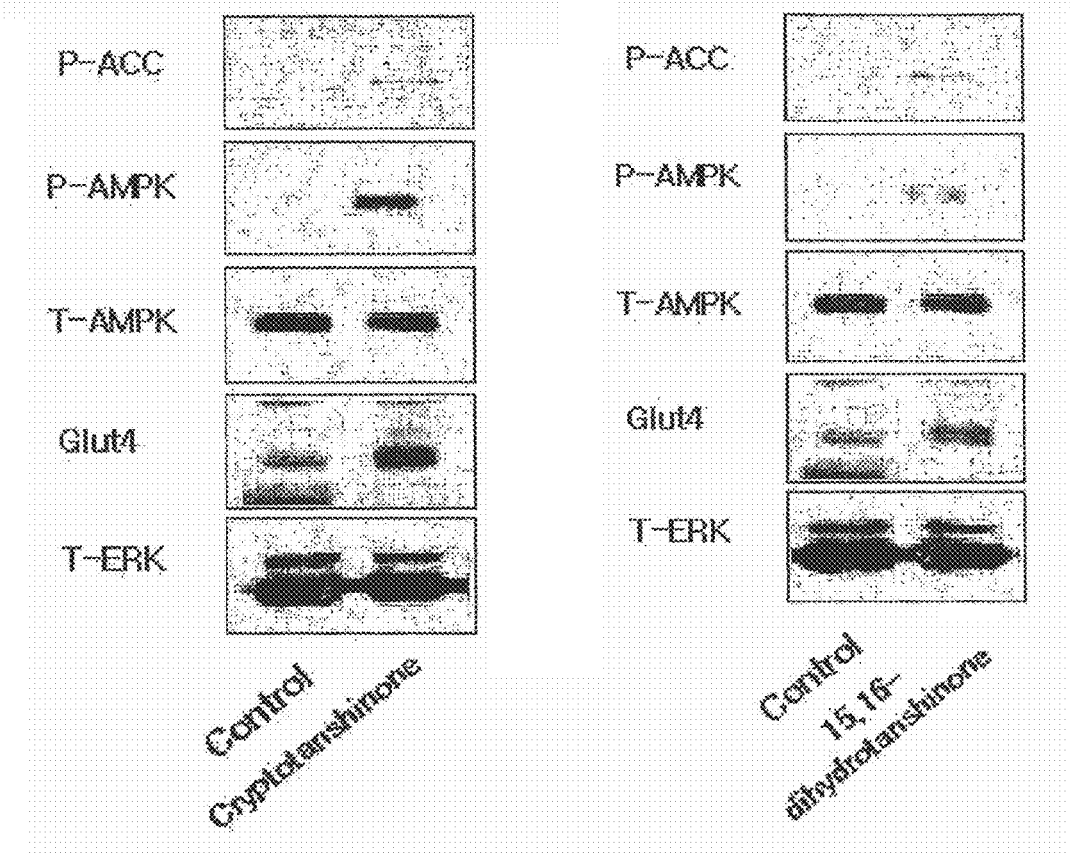
FIG. 2 shows results of Western blotting to determine effects of tanshinone derivatives on protein expression of total AMPK, p-AMPK, p-ACC and GLUT4, after treatment of myoblast cell line C2C12 with tanshinone derivatives.

As can be seen from FIG. 2, when comparing with the control group, tanshinone derivative-treated cells exhibited increased amount of the phosphorylated AMPK protein, increased amount of the phosphorylated A C protein and increased expression level of GLUT4 protein, even though there was no change in the total amount of AMPK protein.

Example 5

Effects of Tanshinone Derivative on Fatty Acid Metabolism and Biosynthesis of Mitochondria Myoblast cells, C2C12 were cell cultured in DMEM containing 10% bovine calf serum. When cell density reached a range of about 85% to 90%, the culture medium was replaced with 1% bovine calf serum medium to induce cellular differentiation. Differentiated cells were treated with 30 μM tanshinone derivatives, respectively. RNAs were extracted from cells and RT-PCR was performed to observe effects of respective tanshinone derivatives on gene expression of ACC-1 (acetyl-CoA carboxylase-1), ACC-2, CPT1 (carnitine palmitoyltransferase I), PGC 1a (peroxisome proliferator-activated receptor gamma co-activator 1α), GLUT1 (glucose transporter 1) and UCP-2 (uncoupling protein-2).

As can be seen from FIG. 3, when comparing with the control group, tanshinone derivative-treated cells exhibited increased expression level of genes for ACC-1, ACC-2, CPT1, PGC-1α, UCP-2 and GLUT1.

Example 6

Analysis of the Degree of Glucose Uptake

Myoblast cells, C2C12, were cell cultured in DMEM containing 10% bovine calf serum. When cell density reached a range of about 85% to 90%, the culture medium was replaced with 1% bovine calf serum medium to induce cellular differentiation. Fully differentiated cells were further cultured in Krebs-Ringer Buffer (KRB) containing 5 mM glucose, for an additional 2 hours. Cells were treated with tanshinone derivatives for a predetermined period of time, 0.2 μCi 2-deoxyglucose was added thereto and allowed to stand for 2 min. After removing the KRB buffer, cells were washed with ice-cold physiological saline buffer, and cells were lysed using 0.5 N NaOH, followed by determination of counts per minute (cpm) using a radiation counter. In this case, non-specific uptake of glucose was determined with the KRB buffer containing 10 μM Cytochalasin B and was subtracted from the total value.

As can be seen from FIG. 4, when C2C12 cells were treated with 30 μM tanshinone derivatives, respectively, the thus-treated cells exhibited increased uptake of glucose, compared to the control group.

Example 7

Determination of Adipocyte Differentiation Inhibitory Activity

Preadipocytes, 3T3-L1 and F442A, were cell cultured in DMEM containing 10% bovine calf serum. When cell density of respective preadipocytes reached about 90%, 3T3-L1 cells were treated with Dexamethasone, IBMX, and insulin for about 48 to 55 hours to induce differentiation of adipocytes. Then, the culture medium was replaced with a medium containing fetal calf serum and insulin every 2 days. In the case of F442A cells, when cell density of preadipocytes reached about 90%, the culture medium was replaced with a medium containing 10% fetal calf serum and insulin and the culture medium was replaced every 2 days, so as to induce differentiation of adipocytes. In order to determine inhibitory effects of adipocyte differentiation, cells in the early stages of adipocyte differentiation were treated with tanshinone derivatives, which was extracted from Danshen, in a concentration of 5 to 30 μM, and were compared with the control group. Differentiation of more than 90% of cells into adipocytes took about 12 to 15 days. In order to study activity of the respective fractions, cells were treated for the same period of time as the control group and were observed under microscope to examine efficacy of tanshinone derivative treatment.

FIG. 5 is a micrograph comparing adipocyte differentiation ability between tanshinone derivative-treated group and control group, with respect to induction timing of adipocyte differentiation. In the case of the control group, differentiation of 80 to 90% of F442A cells into adipocytes took about 11 days. Whereas, in the case of tanshinone derivative-treated group, when cells were treated with a concentration of 30 μM tanshinone derivatives from the early stage of differentiation, only 5 to 10% of cells differentiated into adipocytes in the same period of time.

Example 8

Effects of Tanshinone Derivatives on Insulin Sensitivity in Muscle Cells

Myoblast cells, C2C12, were cell cultured in DMEM containing 10% bovine calf serum. When cell density reached a range of about 85% to 90%, the culture medium was replaced with 1% bovine calf serum medium to induce cellular differentiation. By treating differentiated myoblast cells with insulin and tanshinone derivatives separately, or in combination thereof, the degree of glucose uptake with respect to various concentrations of the tanshinone derivatives was determined and thereby effects of tanshinone derivatives on insulin sensitivity were examined.

As can be seen from FIG. 6, when tanshinone derivatives were administered at various concentrations in the presence of insulin, this exhibited facilitated concentration-dependent uptake of glucose into muscle cells, as compared to the group to which insulin alone was administered and the control group.

Example 9

Assay of Obesity Prophylactic and Therapeutic Effects in Animal Model of Obesity, DIO Mouse As the most commonly used mouse model for diet-induced obesity (DIO), 4-week-old C57BL/6 male mice were fed a high-fat diet (D12451, 45% kcal fat, Research Diets, New Brunswick, N.J.).

As a result, fat excessively accumulated in the animal body and about 3 months after birth, the mice then maintained a body weight of more than 31 to 32 g, which is 1.4 times that of normal mice. In order to examine the effects of tanshinone derivatives on fat metabolism, 3-month-old DIO mice (1.6 animals), weighing 31 to 32 g, were divided into two groups, one experimental group and one control group, consisting of 8 animals each. 8 mice of the experimental group were administered tanshinone derivatives at a concentration of 100 mg/kg, for 30 days, at a predetermined time point. Whereas, the control group was administered an equal amount of distilled water alone. When the body weights of the experimental group and control group were measured after 30 days of administration, the experimental group to which tanshinone derivatives was administered exhibited significantly lower body weight, as compared to the control group, as shown in FIG. 7.

Example 10

Effects of Tanshinone Derivative Administration on Obese Mice (ob/ob)

10-week-old C57BL/6JL Lep ob/Lep ob male mice having obesity characteristics were purchased from Daehan Biolink Co., Ltd. (Chungchongbuk-do, Korea). Animals were raised in a breeding room maintained at a temperature of 23 C, 55% humidity, illumination of 300 to 500 lux, a light-dark cycle of 12:12 hours, and ventilation of 10 to 18 times/hr. Animals were fed pellets of Purina Rodent Laboratory Chow 5001 (purchased from Purina Mills Inc., St. Louis, Mo., USA) and water ad libitum. Mice were allowed to acclimate to new environment of the breeding room for two weeks and were administered 300 mg/kg of tanshinone derivatives for 26 days. Observation was made on changes in body weight, blood glucose and dietary intake, with respect to time points of administration. After completion of administration, computed Tomography (CT) was performed to confirm changes in fat tissue distribution of animals, changes in fat distribution of tissues in various organs, changes in size of adipocytes, glucose in blood and liver, and changes in lipid and enzymes. The table of FIG. 9 shows body weight loss effects according to administration of tanshinone derivatives.

FIG. 8 is a graph comparing changes in body weight over time, between C57BL/6JL Lep ob/Lep ob mice, to which tanshinone derivatives were administered and a control group. As can be seen from FIG. 8, administration of tanshinone derivatives lead to a significant reduction in body weight, as compared to the control group.

FIG. 10 is a graph comparing adipocyte size in terms of numerical values, between C57BL/6JL Lep ob/Lep ob mice to which tanshinone derivatives were administered and a control group. As can be seen from FIG. 10, the experimental group to which tanshinone derivatives were administered exhibited a reduction of more than 60% in adipocyte size, as compared to the control group.

FIG. 11 is a graph comparing fat distribution in terms of numerical value for respective organs between C57BL/6JL Lep ob/Lep ob mice to which tanshinone derivatives were administered and a control group. As can be seen from FIG. 11, the experimental group to which tanshinone derivatives were administered exhibited a significant reduction in fat content of tissues for all organs, and increased brown fat content compared with the control group, indicating that fat metabolism was significantly increased.

FIG. 12 is a graph comparing adipose tissue distribution in the liver by H&E staining and Oil-Red O staining, for normal mice, obese mice and C57BL/6JL Lep ob/Lep ob mice to which tanshinone derivatives were administered. As shown in FIG. 12, it was confirmed through staining of adipose tissues that administration of tanshinone derivatives resulted in a pronounced reduction of fat accumulation in the liver, as compared to the control group of obese mice.

FIG. 13 is a table showing results for changes in lipid and antioxidation indicator materials in liver tissues between C57BL/6JL Lep ob/Lep ob mice to which tanshinone derivatives were administered and a control group. As can be seen from FIG. 13, the group to which tanshinone derivatives were administered exhibited significant reductions in total fat contents, triglyceride, cholesterol, GOT and OPT in the liver, compared with the control group.

FIG. 14 is a table comparing changes in lipid and glucose in the blood between C57BL/6JL Lep ob/Lep ob mice to which tanshinone derivatives were administered and control group. As can be seen from FIG. 14, the group to which tanshinone derivatives were administered exhibited significant reductions in triglyceride, cholesterol, GOT and glucose in blood, compared with the control group.

FIG. 15 shows analyzed results of computed Tomography (CT) of C57BL/6JL Lep ob/Lep ob mice to which tanshinone derivatives were administered. As can be seen from FIG. 15, the experimental group to which tanshinone derivatives were administered exhibited a significant reduction in visceral fat distribution, compared with the control group.

Example 11

Assay of Diabetes Prophylactic and Therapeutic Effects in Animal Model of Diabetes, Lepr db/Lepr db Mouse Lepr db/Lepr db male mice lack leptin receptors and thus continuously and excessively consume feed due to their uncontrolled appetite. As a result, fat is excessively accumulated in the animal body and blood glucose level is elevated, resulting in about 350 to 400 mg/dl of blood glucose level about 10 to 11 weeks after birth. In order to examine prophylactic and therapeutic effects of diabetes by tanshinone derivatives, adult Lepr db/Lepr db male mice with blood glucose level of about 350 to 400 mg/dl were divided into two groups, one experimental group and one control group, consisting of 10 animals each. 10 mice of the experimental group were administered tanshinone derivatives at a concentration of 300 mg/kg, for 12 days. Whereas, 10 mice of the control group was administered an equal amount of distilled water alone, instead of tanshinone derivatives. FIG. 16 is a table showing changes in blood glucose with respect to administration period of tanshinone derivatives and it can be seen that there were blood glucose-lowering effects by tanshinone derivatives.

Example 12

Synergistic Effects of AMPK Activity with Respect to Combination Ratio Between Tanshinone Derivatives Using muscle cells, this example was carried out to confirm synergistic effects of AMPK activity with respect to the combination ratio between derivatives, which contained tanshinone I, tanshinone IIA, cryptotanshinone and 15,16-dihydrotanshinone I, as main ingredients. That is, we have attempted to confirm inter-complementary functions between derivatives according to gene expression as shown in Example 5 and thereby synergistic effects by any combination of tanshinone derivatives through AMPK activity.

The respective ingredients of tanshinone I, tanshinone IIA, cryptotanshinone and 15,16-dihydrotanshinone I were doubly or triply combined to prepare different compositions. AMPK activity of the prepared compositions and the AMPK activity of respective ingredients included in those compositions were compared to confirm synergistic effects. In addition, we have attempted to confirm AMPK activity with respect to changes in the combination ratio by varying the ratio between ingredients in the compositions, and to obtain synergistic effects of activity by any combination of tanshinone derivatives.

FIG. 17 is a table comparing activity of compositions by double combination of tanshinone derivatives, FIG. 18 is a table showing changes in activity with respect to changes of ingredient ratio in double combinations, and FIG. 19 is a table comparing AMPK activity of compositions by triple combination of tanshinone derivatives.

First, as can be seen from FIGS. 17 and 18, compositions containing a two- or three-component combination of tanshinone derivatives exhibited significantly larger AMPK activity than those of the respective ingredients, at the same concentration. It could be seen that such synergistic effects due to combinations of derivative ingredients are very unique phenomena having no relationship with kinds of ingredients. Whereas, as can be seen from FIG. 18, differences in combination ratio between the respective ingredients in the same compositions resulted in specifically different AMPK activity depending upon kinds of ingredients.

Example 13

Synergistic Effects of Reduction in Body Weight with Respect to Combination Ratio Between Tanshinone Derivatives 10-week-old C57BL/6JL Lep ob/Lep ob male mice having obesity characteristics were purchased from Daehan Biolink Co., Ltd. (Chungchongbuk-do, Korea). Animals were raised in a breeding room maintained at a temperature of 23, 55% humidity, illumination of 300 to 500 lux, a light-dark cycle of 12:12 hours, and ventilation of 10 to 18 times/hr. Animals were fed pellets of Purina Rodent Laboratory Chow 5001 (purchased from Purina Mills Inc., St. Louis, Mo., USA) and water ad libitum. Mice were allowed to acclimate to new environment of the breeding room for two weeks and were administered tanshinone derivatives. Tanshinone derivatives contained in Danshen extracts were divided into two groups: a tetrahydrophenanthrene derivative group (1:1 ratio of cryptotanshinone and tanshinone IIA), and a phenanthrene derivative group (2:1 ratio of tanshinone 1 and 15,16-dihydrotanshinone 1), and the ratio between tanshinone derivatives was optionally adjusted. In this manner, we attempted to examine effects of changes in ingredient ratio on body weight and thus to confirm effects of inter-complementary actions. Combination ratio between the tetrahydrophenanthrene derivative group and phenanthrene derivative group was varied from 10:1 to 1:10 and administered to animals at a dose of 300 mg/kg for 26 days. Changes in body weight with administration of derivatives were measured and body weight reduction effects with respect to changes in the ingredient ratio were shown in FIG. 20. As can be seen from FIG. 20, changes in the combination ratio between the tetrahydrophenanthrene derivative and phenanthrene derivative lead to changes in reduction (%) of body weight. In particular, excellent synergistic effects were confirmed, when the combination ratio (tetrahydrophenanthrene derivative:phenanthrene derivative) was in the range of 5:1 to 1:5 and more preferably, in the range of 2.5:1 to 1:2.5.

Example 14

Acute Toxicity Test

1. Oral Administration

ICR mice, weighing 23±2 g and Sprague-Dawley rats, weighing 250±7 g (Jung-Ang Lab Animal Inc., Seoul, Korea) were divided into 4 groups, consisting of 10 animals each, and were orally administered tanshinone derivatives in accordance with the present invention at doses of 100, 500 and 1,000 mg/kg, respectively. After oral administration, upon observing for 2 weeks whether toxicity was exhibited or not, none of the animals died in all four groups and no visually observable symptoms were noticed compared to the control group (except loss of weights).

2. Peritoneal Administration

ICR mice, weighing 25±3 g and Sprague-Dawley rats, weighing 255±46 g (Jung-Ang Lab Animal Inc., Seoul, Korea) were divided into 4 groups, consisting of 10 animals each, and were peritoneally administered tanshinone derivatives in accordance with the present invention at doses of 10, 50 and 100 mg/kg, respectively. After peritoneal administration, upon observing for 2 weeks whether toxicity was exhibited or not, none of the animals died in all four groups and no visually observable symptoms were noticed compared to the control group (except loss of weights).

It was confined from the above-mentioned results that tanshinone derivatives in accordance with the present invention had no acute toxicity.

Hereinafter, Preparation Examples of the pharmaceutical composition in accordance with the present invention will be described. These examples are provided only for illustrating the present invention and should not be construed as limiting the scope and sprit of the present invention

Example 15

Preparation of Tablet

| | |
|---|---|
| Tanshinone derivatives | 200 g |
| Milk serum protein | 640 g |
| Crystalline cellulose | 140 g |
| Magnesium stearate | 10 g |
| Hydroxypropylmethylcellulose | 10 g |

Example 16

Preparation of Powdered Formulation

| | |
|---|---|
| Tanshinone derivatives | 10 g |
| Soybean protein | 50 g |
| Carboxycellulose | 40 g |
| Total | 100 g |

Example 17

Application of Tanshinone Derivatives to Milk

| | |
|---|---|
| Milk | 99.9% |
| Tanshinone derivatives | 0.1% |

Example 18

Application of Tanshinone Derivatives to Orange Juice

| | |
|---|---|
| Liquid fructose | 5% |
| Polydextrose | 1% |
| Citric acid | 5% |
| Vitamin C | 0.02% |
| Tanshinone derivatives | 0.1% |
| Concentrates of orange fruit juice | 25% |
| Sucrose fatty acid ester | 0.2% |
| Water | 63% |

Example 19

Preparation of Beverage

| | |
|---|---|
| Calcium lactate | 50 mg |
| Citric acid | 5 mg |
| Nicotinic amide | 10 mg |
| Riboflavin sodium hydrochloride | 3 mg |
| Pyridoxine hydrochloride | 2 mg |
| Arginine | 10 mg |
| Sucrose fatty acid ester | 10 mg |
| Tanshinone derivatives | 10 mg |
| Water | 200 ml |

Example 20

Application of Tanshinone Derivatives to Cosmetic Lotion

| | |
|---|---|
| 1,3-butylene glycol | 5% |
| Glycerine | 5% |
| EDTA-2Na | 0.02% |
| Trimethylglycine | 2.0% |
| Cetanol | 1.0% |
| Glyceryl monostearate emulsifier | 1.0% |
| Polysorbate 60 | 1.2% |
| Sorbitan sesquioleate | 0.3% |
| Cetyl 2-ethyl-hexanoate | 4.0% |
| Squalane | 5.0% |
| Dimethicone | 0.3% |
| Glyceryl stearate | 0.5% |
| Carbomer | 0.15% |
| Triethanolamine | 0.5% |
| Imidazolidinyl urea | 0.2% |
| Tanshinone derivatives | 1% |
| Purified water | 71.8% |

Example 21

Application of Tanshinone Derivatives to Cosmetic Skin Care

| | |
|---|---|
| 1,3-butylene glycol | 4.0% |
| Dipropylene glycol | 5.0% |
| EDTA-2Na | 0.02% |
| Octyldodeceth-16 | 0.3% |
| PEG60 hydrogenated castor oil | 0.2% |
| Tanshinone derivatives | 0.1% |
| Purified water | 90% |

INDUSTRIAL APPLICABILITY

As described above, a composition in accordance with the present invention effectively reduces body weight through metabolic activation, prevents fat accumulation in the body, lowers blood glucose level, and effectively decreases amounts of cholesterol and triglyceride, and thus is useful for preventing and treating metabolic syndrome. In addition, the composition prevents fat accumulation in the body, as well as enhances insulin sensitivity, thus controlling blood glucose level, and therefore may be useful in developing foods, cosmetics and medicinal compositions capable of preventing or treating various diseases associated with metabolic syndrome resulting from dysfunction of fat and glucose metabolism.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of treating obesity and metabolic syndrome diseases, comprising
    administering a composition comprising a therapeutically and/or prophylactically effective amount of Danshen (*Salvia miltiorrhiza*) extract,
    wherein the Danshen extract comprises
        cryptotanshinone and tanshinone IIA as tetrahydrophenanthrene derivatives;
        tanshinone 1 and 15,16-dihydrotanshinone I as phenanthrene derivatives; and
        one or more compounds selected from the group consisting of 1β-hydroxycryptotanshinone, 1-oxocryptotanshinone, tanshinol B, tanshinol IIB, przewaquinone A, dihydroisotanshinone I, tanshinone IIA sulfonate, 1,2-dihydrotanshinone I and tanshinone VI;
    wherein the ratio of tetrahydrophenanthrene derivatives: phenanthrenes derivative is in the range of 10:1 to 1:10 (w/w).

2. The method as set forth in claim 1, wherein the ratio of tetrahydrophenanthrene derivatives:phenanthrene derivatives is in the range of 5:1 to 1:5.

3. The method as set forth in claim 1, wherein the ratio between cryptotanshinone and tanshinone IIA is in the range of 1:5 to 5:1 (w/w).

4. The method as set forth in claim 1, wherein the composition comprises cryptotanshinone as the most abundant ingredient.

5. The method as set forth in claim 1, wherein the composition comprises tanshinone IIA as the most abundant ingredient.

6. The method as set forth in claim 1, wherein the metabolic syndrome disease is at least one selected from the group consisting of diabetes, arteriosclerosis, hypertension, hyperlipidemia, hepatic diseases, cerebral apoplexy, myocardial infarction, ischemic diseases and cardiovascular diseases.

7. The method as set forth in claim 1, wherein the composition increases activity of 5' AMP-activated protein kinase (AMPK).

8. The method as set forth in claim 7, wherein the ratio of tetrahydrophenanthrene derivatives:phenanthrene derivatives is in the range of 2.5:1 to 1:2.5.

* * * * *